US008684595B2

(12) United States Patent
Wardle et al.

(10) Patent No.: US 8,684,595 B2
(45) Date of Patent: Apr. 1, 2014

(54) SYSTEMS AND METHODS FOR STRUCTURAL SENSING

(75) Inventors: Brian L. Wardle, Lexington, MA (US); Roberto Guzman de Villoria, Cambridge, MA (US); Antonio Miravete, Southborough, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 113 days.

(21) Appl. No.: 12/943,775

(22) Filed: Nov. 10, 2010

(65) Prior Publication Data

US 2011/0142091 A1     Jun. 16, 2011

Related U.S. Application Data

(63) Continuation-in-part of application No. PCT/ES2009/000280, filed on May 20, 2009.
(60) Provisional application No. 61/259,925, filed on Nov. 10, 2009, provisional application No. 61/262,864, filed on Nov. 19, 2009.

(30) Foreign Application Priority Data

May 20, 2008    (ES) .................................. 200801469

(51) Int. Cl.
*G01N 25/00*     (2006.01)
(52) U.S. Cl.
USPC .............. 374/45; 977/902; 977/932; 977/949
(58) Field of Classification Search
USPC ................... 374/45; 977/949, 950, 953, 956; 73/767, 768, 775, 777, 866
See application file for complete search history.

(56) References Cited

U.S. PATENT DOCUMENTS

| | | |
|---|---|---|
| 3,594,775 A | 7/1971 | Fox |
| 4,170,677 A | 10/1979 | Hutcheson |

(Continued)

FOREIGN PATENT DOCUMENTS

| | | |
|---|---|---|
| WO | WO 2004/065926 A1 | 8/2004 |
| WO | WO 2006/004733 A1 | 1/2006 |

(Continued)

OTHER PUBLICATIONS

Authors: T.J. Ahmed, G.F. Nino, H.E.N. Bersee, and A. Beukers, Title: Heat Emitting Layers as an aid for enhancing NDE of aircraft composites strucutures, Date: Apr. 7, 2008, Conference: 49th AIAA/ASME/ASCE/AHS/ASC Structures, Structural Dynamics and Materials Conference 2008, pp. i and 2081-2089.*

(Continued)

*Primary Examiner* — Lisa Caputo
*Assistant Examiner* — Roger Hernandez-Prewitt
(74) *Attorney, Agent, or Firm* — Wolf, Greenfield & Sacks, P.C.

(57) ABSTRACT

Systems and methods related to the determination of one or more mechanical characteristics of a structural element are generally described. In some embodiments, a mechanical characteristic (e.g., a crack, a deformation, an inclusion, etc.) can be determined based at least in part upon the determination of a temperature generated, for example, by passing a current through a network of structures within the structural element. For example, in some embodiments, the structural element can comprise a network of electrically conductive nanostructures and, in some cases, a primary structural material that is not substantially electrically conductive. An electrical current can be passed through the network of electrically conductive nanostructures (e.g., by passing current through an electrical circuit comprising the network of electrically conductive nanostructures). This may result in resistive heating (also known as Joule-effect heating) of the nanostructure network. In some embodiments, a first temperature of the network and/or structural elements can be determined (e.g., via a sensor associated with the electrical circuit). This first temperature can be, in some cases, indicative of a mechanical characteristic of the structural element. In some embodiments, one or more mechanical characteristics of the structural element can be determined based at least in part upon the determination of the first temperature of the structural element.

64 Claims, 16 Drawing Sheets

(56) References Cited

U.S. PATENT DOCUMENTS

| | | | |
|---|---|---|---|
| 6,180,925 | B1 | 1/2001 | Moore et al. |
| 6,236,025 | B1 | 5/2001 | Berkcan et al. |
| 6,276,214 | B1 | 8/2001 | Kimura et al. |
| 6,514,453 | B2 * | 2/2003 | Vigliotti et al. ............... 264/618 |
| 6,882,051 | B2 * | 4/2005 | Majumdar et al. ............ 257/746 |
| 6,986,853 | B2 | 1/2006 | Glatkowski et al. |
| 7,057,881 | B2 | 6/2006 | Chow et al. |
| 7,106,310 | B2 | 9/2006 | Knowles et al. |
| 7,217,374 | B2 * | 5/2007 | Watanabe et al. ............ 252/502 |
| 7,537,825 | B1 | 5/2009 | Wardle et al. |
| 7,659,493 | B2 | 2/2010 | Reusche et al. |
| 7,673,521 | B2 * | 3/2010 | Ajayan et al. ................... 73/774 |
| 7,786,736 | B2 | 8/2010 | Thostenson et al. |
| 7,968,824 | B2 | 6/2011 | Lee et al. |
| 8,257,678 | B2 | 9/2012 | Steiner, III et al. |
| 8,525,507 | B2 | 9/2013 | Aldraihem |
| 2003/0205671 | A1 | 11/2003 | Thomas et al. |
| 2005/0036905 | A1 * | 2/2005 | Gokturk ......................... 422/55 |
| 2005/0284232 | A1 | 12/2005 | Rice |
| 2006/0169788 | A1 | 8/2006 | Empedocles et al. |
| 2007/0041887 | A1 | 2/2007 | Veedu et al. |
| 2007/0132043 | A1 | 6/2007 | Bradley et al. |
| 2007/0138010 | A1 | 6/2007 | Ajayan |
| 2007/0170170 | A1 | 7/2007 | Sata et al. |
| 2007/0222472 | A1 | 9/2007 | Raravikar et al. |
| 2008/0075954 | A1 | 3/2008 | Wardle et al. |
| 2008/0170982 | A1 | 7/2008 | Zhang et al. |
| 2008/0290080 | A1 | 11/2008 | Weiss |
| 2009/0121727 | A1 | 5/2009 | Lynch et al. |
| 2009/0272935 | A1 | 11/2009 | Hata et al. |
| 2009/0277897 | A1 | 11/2009 | Lashmore et al. |
| 2009/0311166 | A1 | 12/2009 | Hart et al. |
| 2010/0196695 | A1 | 8/2010 | Garcia et al. |
| 2010/0255303 | A1 | 10/2010 | Wardle et al. |
| 2013/0058859 | A1 | 3/2013 | Steiner, III et al. |

FOREIGN PATENT DOCUMENTS

| | | | |
|---|---|---|---|
| WO | WO 2007/136755 | A2 | 11/2007 |
| WO | WO2007136264 | A1 * | 11/2007 ............. G01N 25/72 |
| WO | WO 2008/054541 | A2 | 5/2008 |
| WO | WO 2008/135606 | A1 | 11/2008 |
| WO | WO 2009/029218 | A2 | 3/2009 |
| WO | WO 2009/141472 | A1 | 11/2009 |

OTHER PUBLICATIONS

International Search Report dated Oct. 13, 2009 in PCT/ES2009/000280.

Written Opinion dated Nov. 23, 2010 in PCT/ES2009/000280.

Ahmed, T. J., et. al., "Heat emitting layers for enhancing NDE of composite structures," *Composites Part A*, vol. 39, Issue 6, pp. 1025-1036, Jun. 2008.

Ajayan, P.M. and J.M. Tour, "Nanotube composites," *Nature*. vol. 447, pp. 1066-1068, Jun. 2007.

Barber, D., et al., "Health Monitoring of Aligned Carbon Nanotube (CNT) Enhanced Composites," *Proceedings of the SAMPE Fall Technical Conference*, Wichita, KS, Oct. 19-22, 2009.

Bar-Cohen, Y. "NDE of fiber-reinforced composite materials—A Review," *Mater. Eval.*, vol. 44, pp. 446-454 (1986).

Bar-Cohen, Y., "Emerging NDE Technologies and Challenges at the Beginning of the 3rd Millennium." *Mater. Eval.*, vol. 5, (2000), pp. 17-30.

Barreiro, A, et al., "Subnanometer Motion of Cargoes Driven by Thermal Gradients Along Carbon Nanotubes." *Science*, 320, 775-777 (2008).

Baughman, R. H., et. al., "Carbon Nanotubes—the Route Toward Applications," *Science*, vol. 297, (2002), pp. 787-792.

Beyakrova, E., et al., "Multiscale carbon nanotube-carbon fiber reinforcement for advanced epoxy composites," *Langmuir*, 2007. 23(7): p. 3970-3974.

Boger L, et al., "Load and Health Monitoring in Glass Fibre Reinforced Composites with an Electrically Conductive Nanocomposite Epoxy Matrix," *Composites Science and Technology*, 68 1886-1894 (2008).

Bouvier, C., "Investigating Variables in Thermographic Composite Inspection." *Mater. Eval.* 53 544-551 (1995).

Cebeci, H, et al., "Multifunctional Properties of High Volume Fraction Aligned Carbon Nanotube Polymer Composites with Controlled Morphology," *Composites Science and Technology* 69 2649-2656 (2009).

Coleman, J. N., et. al., "Small but strong: A review of the mechanical properties of carbon nanotube-polymer composites," *Carbon* 44 (9), 1624 (2006).

Dharap, P., et al., "Nanotube film based on single-wall carbon nanotube for strain sensing," *Nanotechnology*, 15, p. 379-82 (2004).

Du, F. M., "Effect of Nanotube Alignment on Percolation Conductivity in Carbon Nanotube/Polymer Composites," *Physical Review B*, vol. 72(12), 121404(R) (2005).

Dzenis, Y., "Structural Nanocomposites," *Science*, 319, pp. 419-420 (2008).

Fernandez, J.E., "Materials for Aesthetic, Energy-Efficient, and Self-Diagnostic Buildings," *Science*, 315, pp. 1807-1810 (2007).

Fiedler, B., et al., "Can Carbon Nanotubes be used to Sense Damage in Composites?" *Annales de Chimie Science des Matériaux* 22 81-94 (2004).

Garcia, E.J., et al., "Fabrication and Multifunctional Properties of High Volume Fraction Aligned Carbon Nanotube Thermoset Composites," *Journal of Nano System & Technology* 1 1-11 (2009).

Garcia, E.J., et al., "Fabrication & Multifunctional Properties of a Hybrid Laminate with Aligned Carbon Nanotubes Grown In Situ" *Composites Science & Technology*, 2008.68(9): p. 2034-2041.

Garcia, E.J., et al., "Fabrication of composite microstructures by capillarity-driven wetting of aligned carbon nanotubes with polymers." *Nanotechnology*, 2007. 18(16): p. 165602.

Garcia, E.J., et al., "Fabrication and Testing of Long Carbon Nanotubes Grown on the Surface of Fibers for Hybrid Composites." in *47th AIAA/ASME/ASCE/AJS/ASC Structures, Structural Dynamics, and Materials Conference*. 2006. Newport, R.I.

Garcia, E.J., et al., "Long Carbon Nanotubes Grown on the Surface of Fibers for Hybrid Composites," *AIAA Journal*, vol. 46, No. 6, 2008, pp. 1405-1412.

Giorleo, G., et al., "Location and Geometry of Defects in Composite Laminates from Infrared Images," *Journal of Materials and Performance*, vol. 7, pp. 367-374 (1998).

Giorleo, G. et al, "Comparison Between Pulsed and Modulated Thermography in Glass—Epoxy Laminates.," *NDT & E International*, vol. 35, pp. 287-292 (2002).

Gojny, F.H., et al., "Carbon nanotube-reinforced epoxy-composites: enhanced stiffness & fracture toughness at low nanotube content." *Composites Science & Technology*, 2004. 64(15): p. 2363-2371.

Goldfine, N., et al., "Conformable Eddy Current Sensors and Methods for Gas Turbine Inspection and Health Monitoring," *Gas Turbine Materials Technology* 105-114 (1999).

Goldfine, N., et al, "Conformable Eddy-Current Sensors and Arrays for Fleetwide Gas Turbine Component Quality Assessment," ASME Turbo Expo Land, Sea, & Air, Jun. 4-7, 2001, New Orleans, Louisiana.

Goldfine, N., et al, "Conformable Eddy-Current Sensors and Arrays for Fleetwide Gas Turbine Component Quality Assessment," *Journal of Engineering for Gas Turbines and Power*, vol. 124, (2002), pp. 904-909.

Guzman De Villoria, R., et al., "High-Yield Growth of Vertically Aligned Carbon Nanotubes on a Continuously Moving Substrate," 2009 *Nanotechnology* 20 405611 (8pp).

Guzman De Villoria, R. et al., "Mechanical model to evaluate the effect of the dispersion in nanocomposites," *Acta Mater.* 55 (9), 3025 (2007).

Hogg, P.J., "Composites in Armor," *Science*, 314, pp. 1100-1101 (2006).

Hou, T.-C., Loh, K. J., and Lynch, J. P., "Spatial Conductivity Mapping of Carbon Nanotube Composite Thin Films by Electrical Impedance Tomography for Sensing Applications," *Nanotechnology* 18, 315501 (9pp) (2007).

(56) References Cited

OTHER PUBLICATIONS

Hung Y. Y, et al., "Review and Comparison of Shearography and Active Thermography for Nondestructive Evaluation," *Materials Science and Engineering: R*, 64, pp. 73-112 (2009).

Jeong, Y. J. et al., "Synergistic Strengthening Effect of Ultrafine-Grained Metals Reinforced with Carbon Nanotubes," *Small*, vol. 3, Issue 5, pp. 840-844 (2007).

Kessler S., et al., "Damage detection in composite materials using Lamb wave methods," *Smart Materials and Structures*, vol. 11, pp. 269-278 (2002).

Koerner, H., et al., "Remotely Actuated Polymer Nanocomposites—Stress-Recovery of Carbon-Nanotube-Filled Thermoplastic Elastomers," *Nature Materials*, vol. 3, pp. 115-120 (2004).

Kupke, M., et al., "Non-Destructive Testing of FRP by D.C. and A.C. Electrical Methods," *Composites Science and Technology*, vol. 61, pp. 837-847 (2001).

Li, C., E.T. Thostenson, and T.-W. Chou, "Sensors and actuators based on carbon nanotubes and their composites: A review." *Composites Science and Technology*, 2008, 68(6): p. 1227-1249.

Li, Z. Q., et al., "Solution of Transient Temperature Field for Thermographic NDT Under Joule Effect Heating," *Journal of Heat Transfer* 127 (7), 670 (2005).

Loh, K., et al., "Carbon Nanotube Sensing Skins for Spatial Strain and Impact Damage Identification," *Journal of Nondestructive Evaluation*, 28 (1), 9 (2009).

Mieres, J.M., et al., "Description of a Traffic Bridge of the Cantabrian SpeedWay Made of Composite Materials," *Materiales de Construcción* vol. 56, pp. 81-86, (2006).

Miravete, A., et al., "Corrosion Study of Fiberglass Rebars Embedded in Concrete: One Case Study," *Corrosion 2007 (NACE International)*, Mar. 11-15, 2007, Nashville, TN. p. 07534.

Musso, S., et al., "Influence of carbon nanotubes structure on the mechanical behavior of cement composites," *Compos. Sci. Technol.*, 69, pp. 1985-1990 (2009).

Nofar, M. et al. "Failure detection and monitoring in polymer matrix composites subjected to static and dynamic loads using carbon nanotube networks," *Composites Science and Technology* 69, (2009) pp. 1599-1606.

Pop, E. et al., "Thermal Conductance of an Individual Single-Wall Carbon Nanotube above Room Temperature," *Nano Lett.* 6 (1), pp. 96-100, (2006).

Qiu, J., et al., "Carbon nanotube integrated multifunctional multiscale composites," *Nanotechnology*, 2007. 18(27): p. 275708.

Raghavan, A., et al., "Structural Health Monitoring using Carbon Nanotube (CNT) Enhanced Composites," *7th International Workshop on SHM (IWSHM07)*, Stanford University, Sep. 9-11, 2009.

Roach, D., "Assessing conventional and advanced NDI for composite aircraft," *High-Performance Composites* 16 (4), 72 (2008).

Sakagami, T., et al., "Applications of pulse heating thermography and lock-in thermography to quantitative nondestructive evaluations," *Infrared Physics & Technology* 43, Vols. 3-5, pp. 211-218 (2002).

Sakagami, T., et al., "New Flaw Inspection Technique Based on Infrared Thermal Images under Joule Effect Heating," *JSME International Journal, Series A: Mechanics and Material Engineering* 37 (4), pp. 380-388 (1994).

Salvetat, J.-P., et al., "Elastic and Shear Moduli of Single-Walled Carbon Nanotube Ropes," *Physical Review Letters*, 82(5): pp. 944-947 (1999).

Schulte, K. and A.H. Windle, "Editorial," *Composites Science and Technology* Carbon Nanotube (CNT)—Polymer Composites, 2007. 67(5): p. 777.

Staszewski, W. J., et al., "Fatigue crack detection in metallic structures with Lamb waves and 3D laser vibrometry," *Measurement Science & Technology*, 2007. 18(3): p. 727-739.

Thostenson, E.T., et al., "Real-time in situ sensing of damage evolution in advanced fiber composites using carbon nanotube networks" *Nanotechnology*, 2008, 19(21): p. 215713.

Thostenson, E.T., et al., "Nanocomposites in Context," *Composites Science and Technology*, vol. 65(3-4):491-516, 2005.

Thostenson, E.T., T.-W.Chou, "Carbon Nanotube Networks: Sensing of Distributed Strain and Damage for Life Prediction and Self-Healing." *Advanced Materials*, 2006. 18(21): p. 2837-2841.

Thostenson, E.T., Z. Ren, and T.-W. Chou, "Advances in the science and technology of carbon nanotubes and their composites." *Composites Science & Technology*, 2001. 61(13): p. 1899-1912.

Treacy, M. M. J., et al, "Exceptionally high Young's modulus observed for individual carbon nanotubes." *Nature*, 1996. 381(6584): p. 678-680.

Triantafillou, T. C., "Strengthening of Structures with Advanced FRPs," *Progress in Structural Engineering and Materials*, 1, pp. 126-134 (1998).

Vaia, R. et al., "Adaptive Composites," *Science* 319, 420-421 (2008).

Veedu, V.P., et al., "Multifunctional composites using reinforced laminae with carbon-nanotube forests." *Nature Materials*, 2006. 5(6): p. 457-462.

Wardle B, et al., "Fabrication and Characterization of Ultrahigh-Volume-Fraction Aligned Carbon Nanotube-Polymer Composites" *Advanced Materials*, vol. 20, pp. 2707-2714 (2008).

Wardle, B.L., et al., "Particle and Fiber Exposures During Processing of Hybrid Carbon-Nanotube Advanced Composites." in *2008 SAMPE Fall Technical Conference*. Sep. 2008. Memphis, TN.

Wei, B.Q., et al., "Reliability and current carrying capacity of carbon nanotubes." *Applied Physics Letters*, 2001. 79(8): p. 1172-1174.

Weritz, F., et al., "Investigation of Concrete Structures with Pulse Phase Thermography," *Materials and Structures*, 38 (2005), pp. 843-849.

Wicks, S.S., et al., "Interlaminar and Intralaminar Reinforcement of Composite Laminates with Aligned Carbon Nanotubes.," *Composite Science and Technology*, vol., 70, pp. 20-28 (2010).

Wicks, S.S., et al. "Fracture Toughness of a Woven Advanced Composite Reinforced with Aligned Carbon Nanotubes." in *50th AIAA/ASME/ASCE/AHS/ASC Structures, Structural Dynamics, and Materials Conference*. 2009. Palm Springs, CA.

Yamamoto, N., et al., "Mechanical, Thermal, and Electrical Properties of Woven Laminated Advanced Composites Containing Aligned Carbon Nanotubes," *17th International Conference on Composite Materials (ICCM)*, Edinburgh, Scotland, Jul. 27-31, 2009.

Yamamoto, N. et al., "High-yield growth and morphology control of aligned carbon nanotubes on ceramic fibers for multifunctional enhancement of structural composites." *Carbon* 47 (3), 551 (2009).

Yi, Y. B., et al., "Statistical geometry of random fibrous networks, revisited: Waviness, dimensionality, and percolation." *Journal of Applied Physics*, 96(3), pp. 1318-1327 (2004).

Yu, M.-F., et al., "Strength and Breaking Mechanism of Multiwalled Carbon Nanotubes Under Tensile Load," *Science*, 287(5453), pp. 637-640 (2000).

Zahn M, "Optical, Electrical and Electromechanical Measurement Methodologies of Fields, Charge and Polarization in Dielectrics," *IEEE Transactions on Dielectrics and Electrical Insulation*, vol. 5, No. 5, pp. 627-650, Oct. 1998.

Zhang, W., et al., "Carbon nanotube/polycarbonate composites as multifunctional strain sensors." *Journal of Nanoscience and Nanotechnology*, 2006. 6: p. 960-4.

Zhu, J., et al., "Processing a glass fiber reinforced vinyl ester composite with nanotube enhancement of interlaminar shear strength." *Composites Science and Technology*, 2007. 67(7-8): p. 1509-1517.

Invitation to Pay Additional Fees issued in International Application No. PCT/US2011/022625, mailed May 13, 2011.

International Search Report issued in International Application No. PCT/US2011/022625, mailed Jul. 28, 2011.

International Preliminary Report on Patenability issued in International Application No. PCT/US2011/022625, issued Jul. 31, 2012.

\* cited by examiner

SYSTEMS AND METHODS FOR STRUCTURAL SENSING

RELATED APPLICATIONS

This application claims the benefit of U.S. Provisional Patent Application Ser. No. 61/259,925, filed Nov. 10, 2009, and entitled "Systems and Methods for Structural Sensing," and U.S. Provisional Patent Application Ser. No. 61/262,864, filed Nov. 19, 2009, and entitled "Systems and Methods for Structural Sensing." This application is also a continuation-in-part of Spanish-language International Patent Application Serial No. PCT/ES2009/000280, filed May 20, 2009, entitled "SISTEMA Y MÉTODO DE MONITORIZACIÓN DEL DAÑO EN ESTRUCTURAS" (In English: "SYSTEM AND METHOD FOR MONITORING DAMAGE TO STRUCTURES"), published as WO/2009/141472 on Nov. 26, 2009, which claims the benefit of Spanish-language Spanish Patent Application Serial No. ES P200801469, filed May 20, 2008, entitled "SISTEMA Y MÉTODO DE MONITORIZACIÓN DEL DAÑO EN ESTRUCTURAS" (In English: "SYSTEM AND METHOD FOR MONITORING DAMAGE TO STRUCTURES"). Each of these applications is incorporated herein by reference in its entirety for all purposes.

FIELD OF INVENTION

Systems and methods related to the determination of one or more mechanical characteristics of a structural element are generally described.

BACKGROUND

The process of implementing a detection and characterization strategy for the determination of mechanical characteristics (e.g., fractures, yields, etc.) of engineering structures is generally referred to as structural health monitoring (SHM). Many techniques such as non-destructive evaluation/inspection (NDE/NDI) and condition-based monitoring can be considered subcategories of SHM. SHM can be used to detect changes to the material and/or geometric properties of a structural system that can, in some cases, adversely affect the system's performance. A typical SHM process can involve the observation of a system over time using periodically sampled measurements from one or more detectors, the extraction of damage-sensitive features from these measurements, and the analysis of these features to determine the current state of system health, making prognoses of system performance in the future, with the view towards making prescriptive recommendations to remedy damage. Present SHM systems can have one or more drawbacks, including relatively poor spatial resolution, inability to detect features within the bulk of the article being analyzed, the need for complex networks of sensors and wires, high power requirements, high cost, and high noise, among others. Accordingly, improved systems, articles, and methods are desirable.

SUMMARY OF THE INVENTION

Systems and methods related to the determination of one or more mechanical characteristics of a structural element are generally described. The subject matter of the present invention involves, in some cases, interrelated products, alternative solutions to a particular problem, and/or a plurality of different uses of one or more systems and/or articles.

In one set of embodiments, a system is described. In some cases, the system can comprise a structural element comprising a network of electrically conductive nanostructures; an electrical circuit comprising at least a portion of the network; and a sensor associated with the electrical circuit, constructed and arranged to determine a first temperature of the structural element and/or of the network.

In another set of embodiments, a method is described. The method can comprise, in some embodiments, providing a structural element comprising a network of electrically conductive nanostructures; passing an electrical current through at least a portion of the network of electrically conductive nano structures; determining a first temperature of the structural element; and determining a mechanical characteristic of the structural element and/or of the network based at least in part upon the first temperature of the structural element.

The method can comprise, in some cases, providing a structural element comprising a primary structural material that is not substantially electrically conductive and a network of electrically conductive nanostructures within the primary structural material, and passing an electrical current through at least a portion of the network of electrically conductive nanostructures. In some instances, the method can further comprise determining a first temperature of the structural element and/or of the network, indicative of resistive heating of the network, thereby determining a mechanical characteristic of the structural element indicative of a mechanical transformation.

In some cases, the method can comprise providing a structural element formed of a primary structural material that is not substantially electrically conductive, and passing an electrical current through at least a portion of the structural element. In some cases, the method can further comprise determining a first temperature of the structural element, and determining a mechanical characteristic of the structural element indicated by the first temperature of the structural element.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
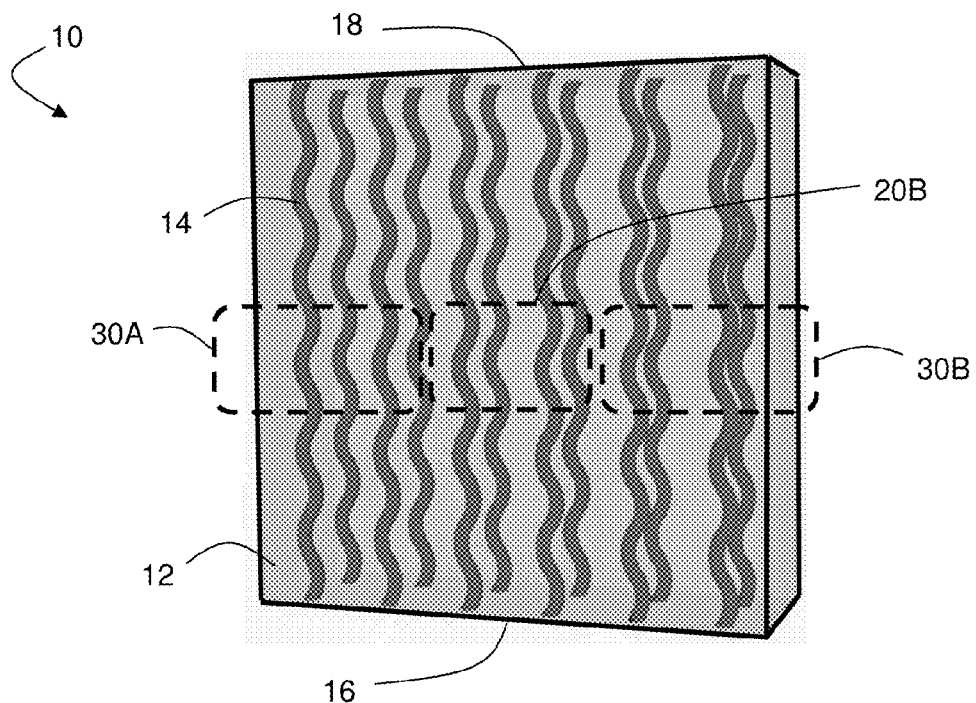
FIGS. 1A-1B include exemplary schematic diagrams illustrating articles and methods for determining mechanical characteristics of a structural element comprising a network of electrically conductive nanostructures.

Systems and methods related to the determination of one or more mechanical characteristics of a structural element are generally described. In some embodiments, a mechanical characteristic (e.g., a crack, a deformation, an inclusion, etc.) can be determined based at least in part upon the determination of a temperature, for example, generated by passing a current through at least a portion of a network of electrically conductive nanostructures within the structural element. In some embodiments, the structural element can carry or envelop a network of electrically conductive nanostructures and, in some cases, a primary structural material that is not substantially electrically conductive. An electrical current can be passed through the network of electrically conductive nanostructures, for example, by passing current through an electrical circuit comprising at least a portion of the network of electrically conductive nanostructures. This may result in resistive heating (also known as Joule-effect heating) of at least a portion of the network of electrically conductive nanostructures and/or at least a portion of the structural element. In some embodiments, a first temperature of the network of electrically conductive nanostructures and/or structural element can be determined (e.g., via a sensor associated with the electrical circuit). This first temperature can be, in some cases, indicative of a mechanical characteristic of the structural element. In some embodiments, one or more mechanical characteristics of the structural element can be determined based at least in part upon the determination of the first temperature of the structural element.

In some embodiments, one or more mechanical characteristics of the structural element can be determined based at least in part upon the gradients in temperature of the structural element. For example, in some embodiments, elements that have not undergone a structural transformation can exhibit no temperature gradient when an electrical current is passed through at least a portion of the element. In some embodiments, elements that have undergone a structural transformation can exhibit a temperature gradient when an electrical current is passed through at least a portion of the element.

Advantageously, the systems and methods described herein can be used to determine a mechanical characteristic of structural element without compromising the structural integrity (e.g., via drilling, fracturing, deforming, etc.) of the structural element. In addition, the systems and methods described herein can be operated relatively inexpensively and by using a relatively low amount of power. The systems and methods described herein can be operated without the use of complex wiring and/or sensor arrangements, and heating sources (e.g., networks of electrically conductive nanostructures) can be relatively easily positioned, in some cases. In addition, the systems and methods described herein can be used without large, generally high-power, external heating sources. As mentioned above, mechanical characteristics within the bulk of the structural element (in addition to mechanical characteristics at an external or internal surface) can be determined, in some embodiments. Also, the systems and methods described herein can be used to determine steady state and/or time-dependent mechanical characteristics of structural elements. In some cases, the systems and methods described herein can be used to make real-time in situ determinations. In addition, electrically conductive nanostructures used in some embodiments can enhance one or more mechanical properties of the structural element. The systems and methods described herein may also provide one or more practical advantages during use. For example, the systems and methods described herein can be used to remove ice from and/or inhibit the formation of ice on a component (e.g., an airplane wing) while determining a mechanical characteristic of the component.

The systems and methods described herein may find application in a variety of fields. For example, some embodiments may be useful in performing non-destructive analysis as part of, for example, a structural health monitoring program, non-destructive evaluation such as condition-based monitoring, and non-destructive inspection such as during manufacturing of a structure (e.g., machining of windows in the composite fuselage of an aircraft). Examples of suitable structural elements that could be analyzed include, but are not limited to, components of bridges, buildings, automobiles, wind turbines (e.g., blades), airplanes, and the like.

The phrase "structural element," as used herein, refers to an article that is designed to support a mechanical load. In some embodiments, the structural element may be designed to support a mechanical load that is external to the structural element. Examples of such structural elements include, but are not limited to, window frames, bridge trellises, steel beams, airplane wings, aerodynamic surfaces, components thereof, and the like. In some cases, the structural element may be designed to support a mechanical load imparted by the structural element itself. In some embodiments, failure of the structural element may lead to the failure of a larger system that incorporates the structural element. In some cases, failure of the structural element can lead to the loss of a nonmechanical function of the structural element.

As used herein, a "network of electrically conductive nanostructures" generally refers to an arrangement of nanostructures in electrical communication with each other such that electrical current can be passed through the network. In some embodiments, the electrically conductive nanostructures within the network may be in direct contact with each other. In some cases, the electrically conductive nanostructures within the network are not in direct contact with each other, but are sufficiently close such that the resulting network is electrically conductive. In some embodiments, the electrical conductivity of a network of electrically conductive nanostructures can be inhibited (e.g., reduced or eliminated) by, for example, the introduction of a fracture, an inclusion, a plastic deformation, an elastic deformation (as might be determined, for example, in strain sensing), a separation of two surfaces, and the like.

A variety of mechanical characteristics of a structural element and/or a network of electrically conductive nanostructures can be determined using the systems and methods described herein. As used herein, a "mechanical characteristic" of an article refers to a feature of the article related to the arrangement of atoms within the article. In some embodiments, a mechanical characteristic can be a defect. In some cases, a mechanical characteristic can be a deformation, including permanent or temporary deformations. Examples of mechanical characteristics include, but are not limited to, cracks, delaminations, dislocations, inclusions, plastic deformations, elastic deformations, surface separations, and the like. In some embodiments, the systems, articles, and methods described herein can be used to determine mechanical characteristics that can be relatively difficult to determine using traditional methods. As one example, the systems and methods described herein can be used to determine a kissing debond (i.e., an interface where a crack exists, but the two surfaces on either side of the crack are in physical contact, for example, due to an applied force), for example, in a laminated composite.

In some embodiments, a mechanical characteristic of a structural element can be indicative of a mechanical transformation. As used herein, the term "mechanical transformation" refers to a process by which an article is transformed from a first mechanical state to a second mechanical state, such that there is at least one substantial difference in the arrangement of atoms within the article in the first mechanical state relative to the second mechanical state. Examples of mechanical transformations include, but are not limited to, bending, yielding, fracturing, and the like.

The term "determining," as used herein, generally refers to the analysis or measurement of an entity (e.g., a mechanical characteristic, for example, of a structural element and/or of a network of electrically conductive nanostructures, etc.) quantitatively or qualitatively, and/or the detection of the presence or absence of an entity. In some embodiments, determining a mechanical characteristic of an entity can comprise determining the location (e.g., a point, a region) of the entity, the size of the entity, or both. In some cases, determining an entity (e.g., a mechanical characteristic of a structural element and/or of a network of electrically conductive nanostructures) can comprise determining the presence or absence of the entity (e.g., within any part of the structural element or within a specific region of the structural element). In addition, an entity such as a mechanical characteristic or network of electrically conductive nanostructures can be determined on an external surface of a structural element, within the bulk of a structural element, or both.

Figure 1B:
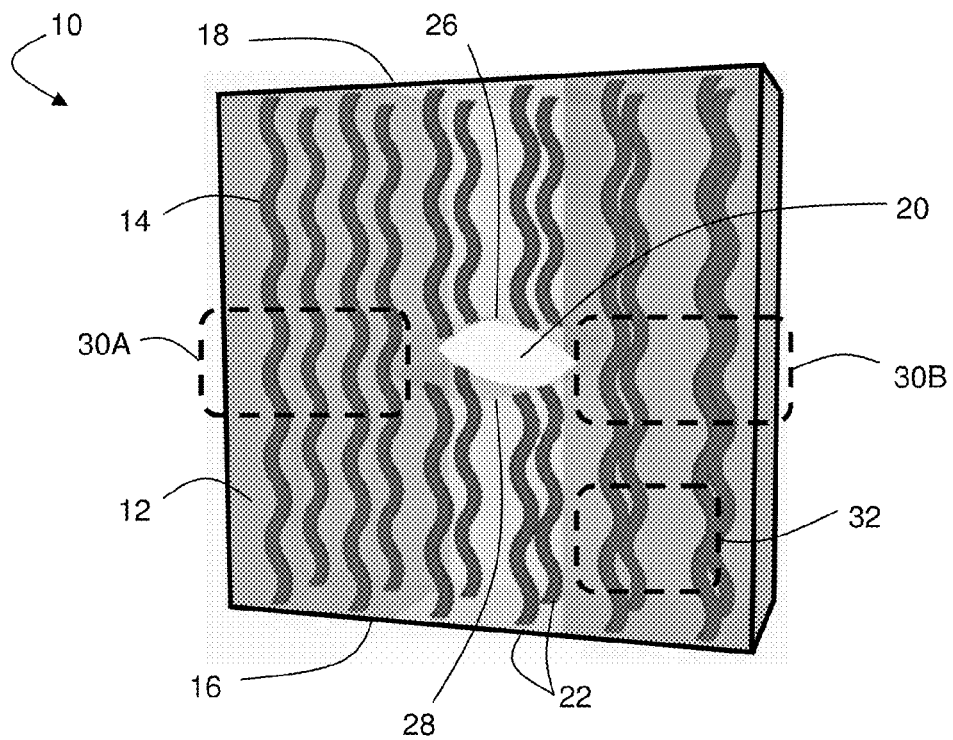

In one set of embodiments, methods for determining one or more mechanical characteristics of structural elements are described. FIGS. 1A-1B include exemplary schematic illustrations outlining the determination of a mechanical characteristic of structural element 10. In this set of embodiments, structural element 10 comprises a primary structural material 12 and a plurality of electrically conductive nanostructures 14. As used herein, the term "nanostructure" refers to articles having at least one cross-sectional dimension, as measured between two opposed boundaries of the nanostructure, of less than about 1 micron. Examples of nanostructures suitable for use in the embodiments described herein include nanotubes (e.g., carbon nanotubes such as single-wall carbon nanotubes and multi-wall carbon nanotubes), nanowires (e.g., carbon nanowires, metal nanowires), nanofibers (e.g., carbon nanofibers, metal nanofibers), graphene nanostructures, graphite nanostructures, nanoparticles (e.g., metal nanoparticles, carbon black nanoparticles, graphite nanoparticles, graphene nanoparticles, etc.), and the like.

In addition, a variety of primary structural materials can be used in the embodiments described herein. In some embodiments, the structural element can include a primary structural material that is not substantially electrically conductive. As used herein, a material is not substantially electrically conductive if it is not electrically conductive at a level sufficient to achieve the determinations described herein. In some such embodiments, the electrically conductive nanostructures within the structural element can increase the electrical conductivity of the structural element relative to the electrical conductivity of the primary structural material in the absence of the electrically conductive nanostructures, but under otherwise essentially identical conditions. Examples of such substantially non-electrically conductive primary structural materials include, but are not limited to, non-conductive monomers, non-conductive polymers (e.g., epoxies, thermosets, thermoplastics, etc.), non-conductive fibers (e.g., alumina fibers), non-conductive woven fabrics (e.g., alumina cloth), non-conductive carbon-fiber advanced composites, non-conductive ceramics, and the like. Of course, it should be understood that, in some cases, the structural elements described herein may include an electrically conductive primary structural material such as, for example, a metal.

In some embodiments, the plurality of electrically conductive nanostructures can define a network through which an electrical current can be passed. In the set of embodiments illustrated in FIGS. 1A-1B, electrically conductive nanostructures 14 span the length of structural element 10 from wall 16 to wall 18. Such an arrangement may be observed, for example, in structural elements that comprise substantially aligned, elongated nanostructures (e.g., nanotubes, nanowires, etc.). It should be understood, however, that the nanostructures need not span a length of the structural element. For example, in some embodiments, the structural element can comprise a plurality of nanoparticles dispersed within the primary structural material of the structural element that are sufficiently close such that they form a network of electrically conductive nanostructures. In some cases, such arrangements of electrically conductive nanostructures may be referred to by those of ordinary skill in the art as being beyond the percolation threshold.

An electrical current can be passed through at least a portion of the network of electrically conductive nanostructures (e.g., through the entire network and/or through a portion of the network) by establishing an electrical circuit that comprises at least a portion of the network, in some instances. For example, in the set of embodiments outlined in FIGS. 1A-1B, electrodes can be electrically connected to walls 16 and 18 of the structural element. In some embodiments, at least a portion of the network of electrically conductive nanostructures and/or of the structural element can be heated (e.g., via resistive heating) when electrical current is passed through at least a portion of the network of electrically conductive nanostructures.

In some embodiments, the methods described herein may include determining a temperature of the structural element and/or the network of electrically conductive nanostructures. The structural elements described herein can exhibit a variety of temperature profiles, distributions, and temporal characteristics, depending upon their mechanical state. For example, in the set of embodiments illustrated in FIG. 1A, the electrically conductive nanostructures are distributed relatively evenly throughout the structural element. Such arrangements can produce a relatively uniform electrical resistance throughout the structural element, and a relatively uniform temperature distribution throughout the network of electrically conductive nanostructures and the structural element.

The temperature of a structural element and/or a network of electrically conductive nanostructures may be indicative, in some embodiments, of one or more mechanical characteristics (which can, in turn, be indicative of one or more mechanical transformations) of the structural element and/or network. In FIG. 1B, structural element 10 has undergone a mechanical transformation that has produced discontinuity 20 within the structural element. A mechanical defect (e.g., the discontinuity in FIG. 1B, an inclusion, a plastic deformation, etc.) can produce a variation in the electrical resistance within the bulk of the structural element which can, in turn, produce a variation in temperature upon passing current through at least a portion of the structural element. For example, the discontinuity in FIG. 1B can produce a discontinuity in the conductive pathway through nanostructures 22.

Discontinuities (or other mechanical characteristics) may affect the temperature profile of the network of electrically conductive nanostructures and/or structural element via several mechanisms. For example, the presence of a discontinuity can, in some cases, substantially eliminate the electrical current passed through the portion of the structural element in which the discontinuity is formed. The inability to pass current through a discontinuity can lead to relatively low temperatures within the bulk of the discontinuity, due to the absence of resistive heating. In some cases, electrical current can be passed through the discontinuity, but the resistance of flow is relatively large due to the discontinuity. In such cases, the region comprising the discontinuity may experience a relatively large amount of resistive heating, and thus, may exhibit a relatively high temperature.

In some cases, the edge of a discontinuity may exhibit a relatively high temperature. Not wishing to be bound by any theory, a relatively high temperature may be observed at the edge of a discontinuity due to the reduction of thermal conductivity between locations (e.g., points, regions) on opposite sides of the discontinuity. For example, in FIG. 1B, discontinuity 20 may include a thermally insulating material (e.g., air), relative to the thermal conductivity of the structural element, which may diminish the extent to which heat can be transported from location 28 to location 26. In some cases, a region comprising an edge of a discontinuity may exhibit a lower temperature relative to the temperature that would be observed in that region in the absence of the discontinuity, but under otherwise essentially identical conditions. For example, in some embodiments, one or more edges of discontinuity 20 in FIG. 1B may exhibit a higher temperature than would be observed in region 20B of FIG. 1A when substantially identical voltages are applied across the structural elements. In some embodiments, an edge of a discontinuity may exhibit a higher temperature relative to other portions of the structural element. For example, in some embodiments, one or more edges of discontinuity 20 in FIG. 1B may exhibit a relatively high temperature compared to, for example, region 32.

In some cases, the edge of a discontinuity can exhibit a relatively low temperature. Not wishing to be bound by any particular theory, the edge of the discontinuity can be relatively insulating, therefore reducing the amount of current that passes through it, leading to a relatively low temperature.

A region of a structural element on the periphery of a discontinuity may exhibit, in some instances, a relatively high temperature. Not wishing to be bound by any theory, a relatively high temperature may be observed at the periphery of a discontinuity due to, at least in part, an increase in the amount of current passed through the peripheral region. For example, in FIG. 1B, the presence of discontinuity 20 in the structural element may lead to the redirection of some or all of the current that would have passed through the region occupied by the discontinuity to regions 30A and/or 30B as current is passed from end 16 to end 18. This can result in an increase in current density passing through regions 30A and 30B, and thus, an increase in the temperature of regions 30A and/or 30B.

Figure 2A:
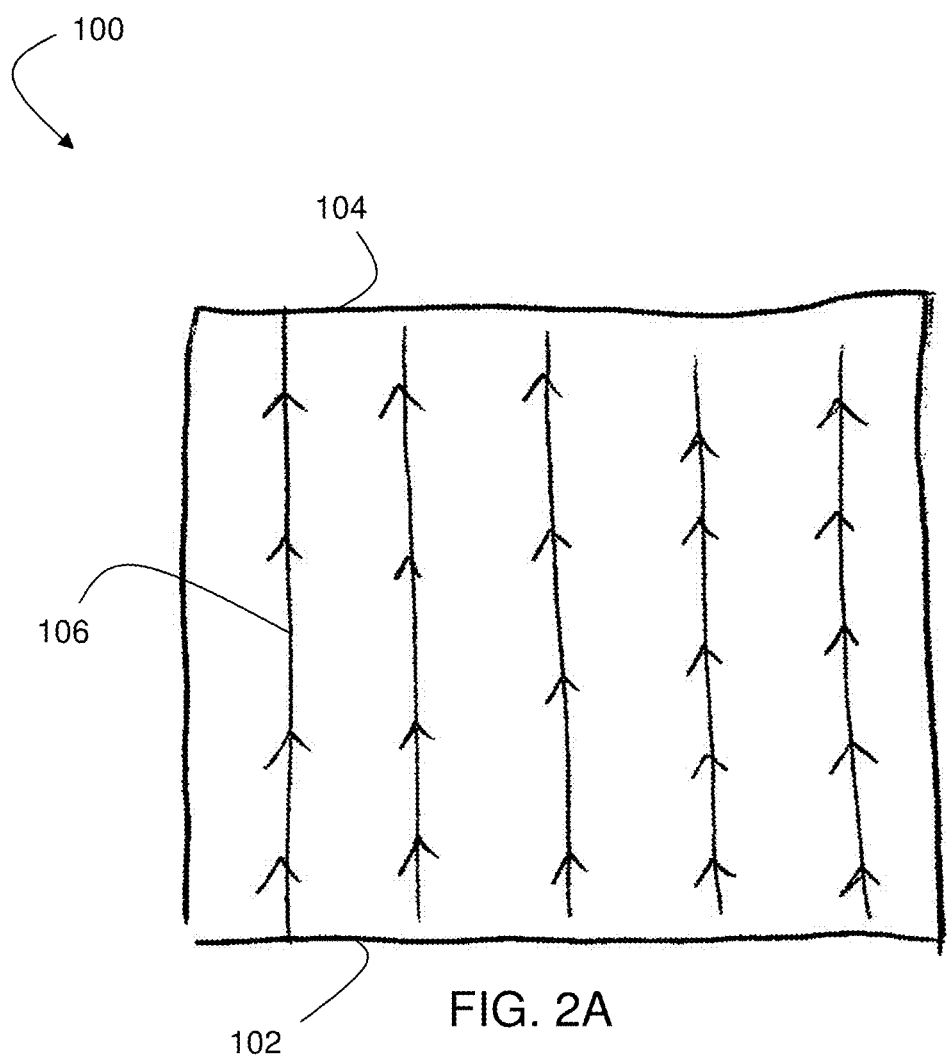
FIGS. 2A-2F include schematic diagrams of structural elements, according to one set of embodiments.
Figure 2B:
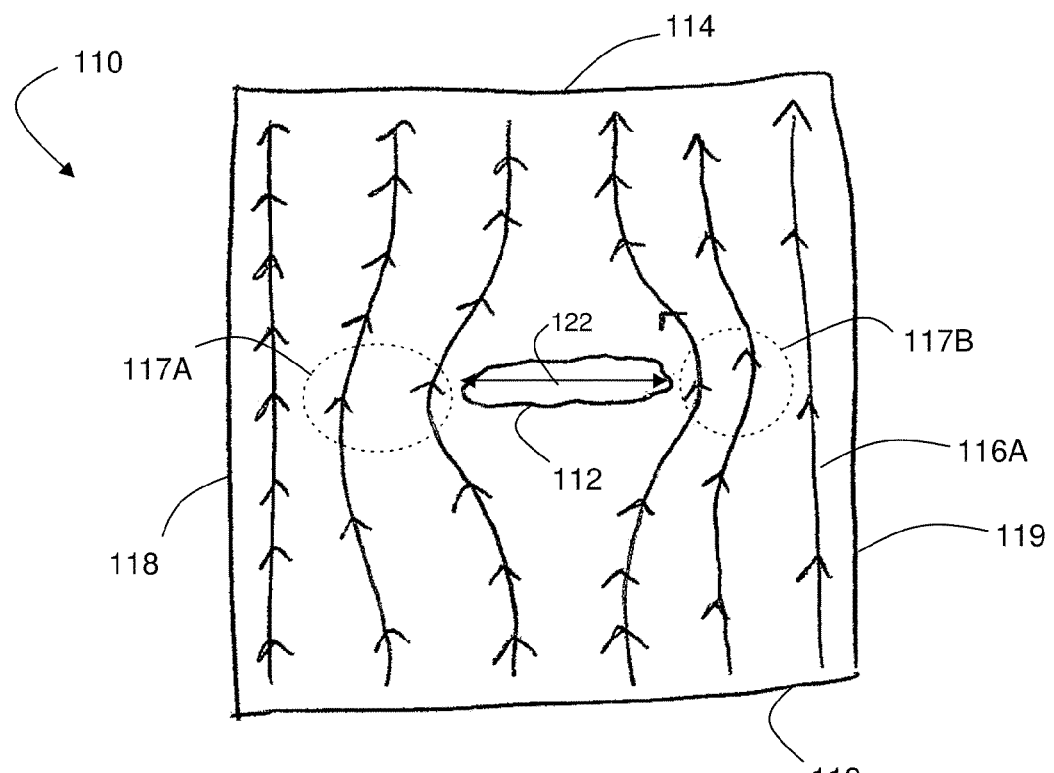
Figure 2C:
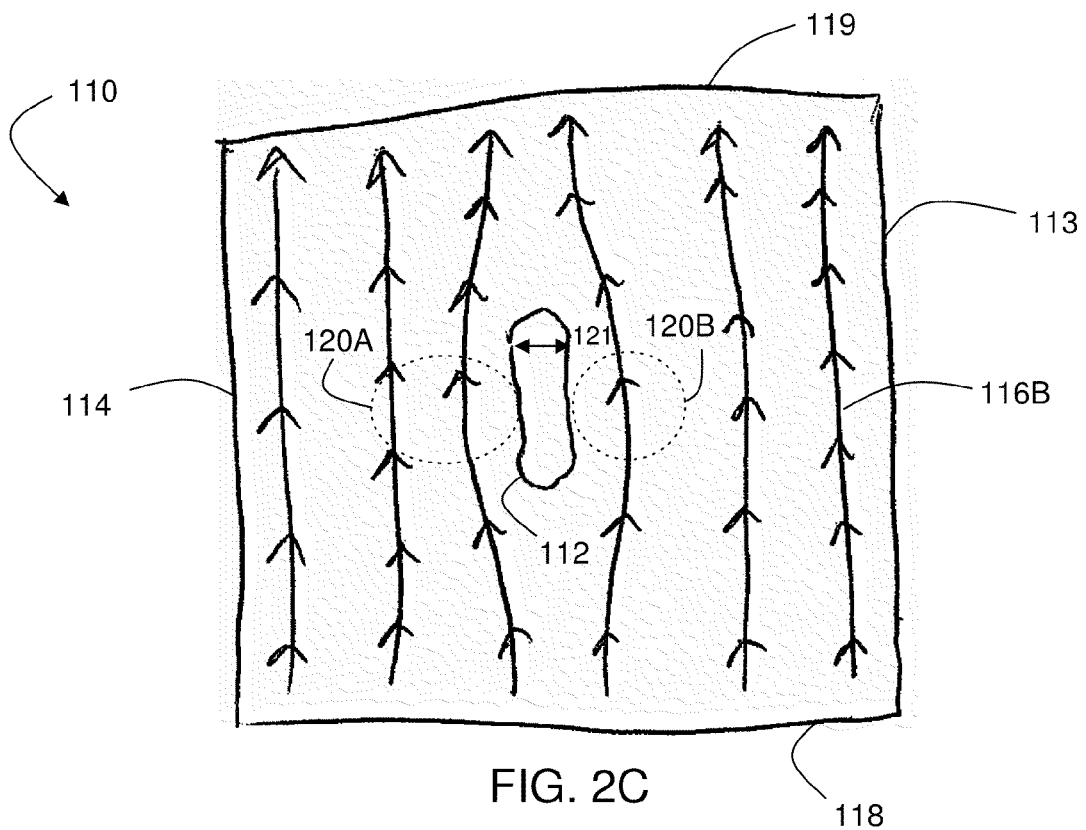

Such effects of mechanical characteristics (e.g., defects) are further illustrated in the exemplary schematic illustrations of FIGS. 2A-2C. In FIG. 2A, structural element 100 is substantially free of defects and includes a relatively uniform distribution of electrically conductive nanostructures (not shown). Accordingly, when a voltage is applied across edges 102 and 104, the field lines of the electrical current (indicated by arrows 106) are relatively uniformly distributed. In FIG. 2B, structural element 110, which also includes a relatively uniform distribution of electrically conductive nanostructures (not shown) within the bulk of the structural article, includes discontinuity 112. Accordingly, when a voltage is applied across edges 113 and 114, the field lines of electrical current 116A can be diverted around the discontinuity, producing two regions 117A and 117B through which a relatively high density of electrical current passes. A similar effect is observed when the structural article is rotated 90 degrees, as shown in FIG. 2C. In the set of embodiments illustrated in FIG. 2C, a voltage is applied across edges 118 and 119, producing regions 120A and 120B through which a relatively high density of electrical current passes. In these cases, the degree to which the electric field lines 116B are diverted is less pronounced than the diversion observed in FIG. 2B because, in FIG. 2C, the dimension of discontinuity 112 that is perpendicular to current flow (indicated by dimension 121) is relatively small compared to the dimension of discontinuity 112 that is perpendicular to current flow in FIG. 2B (indicated by dimension 122).

In some embodiments, a region of a structural element on the periphery of a discontinuity may exhibit a higher temperature relative to the temperature that would be observed in that region in the absence of the discontinuity, but under otherwise essentially identical conditions. For example, referring back to the exemplary embodiments of FIGS. 1A-1B, peripheral regions 30A and/or 30B in FIG. 1B may exhibit a higher temperature than would be observed in regions 30A and/or 30B of FIG. 1A when substantially identical voltages are applied across the structural elements. In some embodiments, a region of a structural element on the periphery of a discontinuity may exhibit a higher temperature relative to other portions of the structural element. For example, in some embodiments, peripheral regions 30A and/or 30B in FIG. 1B may exhibit a higher temperature relative to region 32.

In some cases, an electrical current can be passed across multiple pairs of locations on or within the structural element. By applying electrical current across multiple pairs of locations, one may be able, in some cases, to more easily determine a mechanical characteristic of the structural element, relative to situations in which current is only passed across one pair of locations. In some cases, a first electrical current can be applied across a first pair of two locations defining a first direction, and a second electrical current can be applied across a second pair of two locations defining a second direction. In some cases, the first and second directions can be substantially orthogonal (e.g., as described in relation to FIGS. 2B-2C above). In some cases, the first and second directions can be substantially parallel, or at any other suitable angle relative to each other. In some embodiments, the first and second electrical currents (and/or additional electrical currents) can be applied at the same time. The first and second electrical currents (and/or additional electrical currents) can also, in some cases, be applied at different times. In addition, characteristics can be determined at different times relative to the application of electrical current. For example, a first characteristic can be determined during the application of a first current (e.g., at a first time), and a second characteristic can be determined during the application of a second current (e.g., at a second time that is the same as or different from the first time).

It should be understood that electrical contact can be made with the structural element at any suitable location and, accordingly, a voltage can be applied (e.g., to produce an electrical current) across any two locations of the structural element. For example, in some embodiments, a voltage can be applied across the ends of the structural element by positioning the electrical leads at the ends of the structural element (e.g., as shown in FIGS. 1A-1B and 2A-2C), Such an arrangement can produce an electrical current that is passed from one end of the structural element to the other.

In some embodiments, a voltage can be applied across only a portion of the structural element, for example, by making electrical contact to two regions on a face of the structural element and/or by making electrical contact to two regions on different (e.g., opposite) faces of the structural element. Applying the voltage across only a portion of the structural element can result in electrical current passing through only a portion of the structural element. In some cases, the distance between the regions at which the electrical connections are made to apply the voltage (as measured from the geometric center of the regions at which the electrical connections are made) can be less than about 80%, less than about 70%, less than about 60%, less than about 50%, less than about 40%, or less than about 25%, less than about 10%, or less than about 5% of the maximum cross-sectional dimension of the structural element through which the electrical current is passed.

Figure 2D:
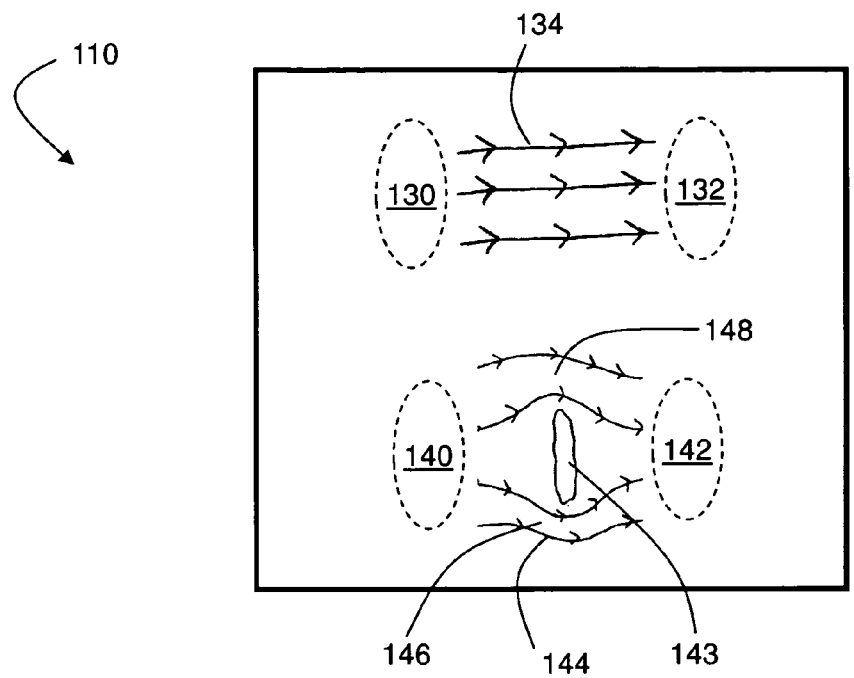

One such set of embodiments is illustrated in FIG. 2D. In this set of embodiments, a voltage is applied between regions 130 and 132 to produce field lines 134 of electrical current. In FIG. 2D, a voltage is also applied between regions 140 and 142 to produce field lines 144 of electrical current around a discontinuity 143. The voltage applied between regions 140 and 142 can be applied at the same time as the voltage between regions 130 and 132, or at a different time (e.g., before or after the voltage between regions 130 and 132 is applied).

The ability to make electrical contact between any two regions of the structural element can allow one to more readily determine the location of a mechanical characteristic such as a discontinuity or other defect, in some instances. For example, in the set of embodiments illustrated in FIG. 2D, field lines 134 are relatively evenly distributed, as there are no structural defects or other characteristics between regions 130 and 132. The presence of the discontinuity between regions 140 and 142, however, can produces relatively dense field lines in regions 146 and 148, which can appear as regions of relatively high temperature, thus indicating the presence of the discontinuity. In some embodiments, electrical connection can be made to more than two pairs of regions, which might be helpful in locating a very small defect within a relatively large structural element.

In some embodiments, electrical contacts can be incorporated into the structural element, which can, for example, expedite the process of applying electrical leads to the structural element. In some embodiments, the electrical contacts can be positioned such that they form a row. For example, in the set of embodiments illustrated in FIG. 2E, structural element 150 includes electrical contacts 152 (e.g., contact pads) arranged in a row along an elongated structural element. A voltage can be readily applied between any two (or more) of the electrical contacts 152 to determine a mechanical characteristic between the electrical contacts.

Figure 2E:
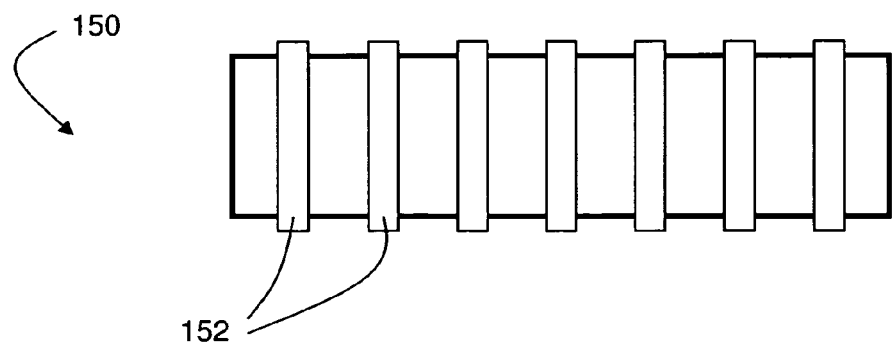
Figure 2F:
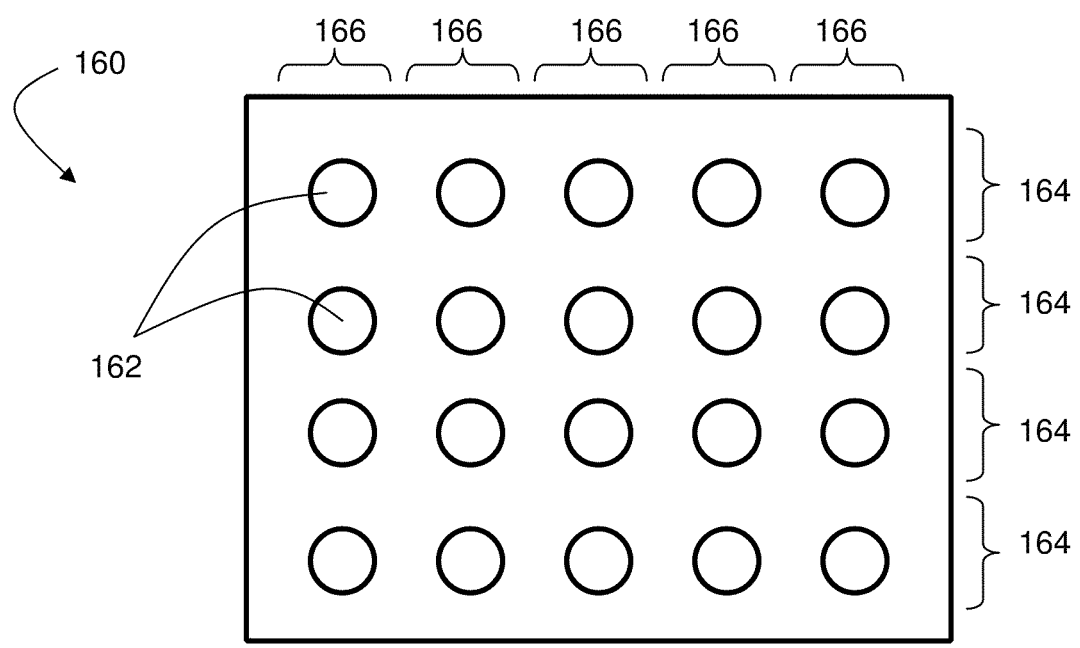

In some instances, the electrical contacts can be arranged in a 2-dimensional or 3-dimensional array (e.g., an arrangement of electrical contact having at least one row and at least one column). For example, in the set of embodiments illustrated in FIG. 2F, structural element 160 includes electrical contacts 162 (e.g., contact pads) arranged to form rows 164 and columns 166. A voltage can be readily applied between any two (or more) of the electrical contacts 162 to determine a mechanical characteristic between the electrical contacts. It should be understood that the layouts of the electrical contacts in FIGS. 2E-2F are exemplary, and a variety of other layouts could be used in association with the embodiments described herein. For example, in some embodiments, two or more electrical contacts can be positioned such that there is a relatively high concentration of electrical contacts at a region that is expected to include a mechanical characteristic (e.g., a defect), relative to regions that are not expected to include a mechanical characteristic. In some cases, two or more electrical contacts can be positioned such that there is a relatively high concentration of electrical contacts at a region that is expected to include a relatively important mechanical characteristic (e.g., a defect), relative to regions that are expected to include no mechanical characteristics and/or less important mechanical characteristics (e.g., characteristics in a benign location).

In some cases, the application of electrical leads to the structural element can be automated (e.g., using a CPU and/or a robotic arm to apply the electrical leads), which can increase efficiency in some embodiments. It should be understood, however, that the invention is not so limited and that, in other cases, the electrical leads can be positioned manually.

While discontinuities have been primarily described, it should be understood that similar principles can be applied to determine other defects (e.g., plastic deformations, inclusions, etc.) or other mechanical characteristics of a structural element (e.g., elastic deformations, etc.). For example, the presence of an inclusion may exhibit similar effects compared to those that would be observed with a discontinuity, for example, when the inclusion comprises a material with a relatively low thermal conductivity compared to the conductivity of the structural element. As another example, an elastic or plastic deformation of an article can lead to an increase or reduction of the electrical resistance within the bulk or on the surface of an article (e.g., via an increase or reduction of a cross-sectional area through which current is applied), which may manifest as a change in temperature relative to a substantially non-deformed structural element or relative to another non-deformed region of the same structural element. One of ordinary skill in the art would be capable of determining, given the present disclosure, the effects of various deformations and defects (and other mechanical characteristics) on the electrical resistance of a structural element, and the corresponding thermal features that would be observed.

In some embodiments, a mechanical characteristic of a structural element can be determined based, at least in part, upon the determination of a first measured temperature of the structural element and/or of the network of electrically conductive nanostructures. One or more temperatures of a structural element can, in some cases, be produced in the absence of a substantial source of heat external to the network of electrically conductive nanostructures. In some cases, one or more temperatures of a structural element can be produced in the absence of a substantial source of heat external to the structural element. In some embodiments, the structural element and/or network of electrically conductive nanostructures can include a maximum temperature at least about 0.01 degrees Celsius, at least about 0.1 degrees Celsius, at least about 1 degree Celsius, at least about 5 degrees Celsius, at least about 10 degrees Celsius, or at least about 15 degrees Celsius hotter than the ambient temperature surrounding the structural element. In some instances, the structural element and/or network of electrically conductive nanostructures can include a maximum temperature at least about 0.01 degrees Celsius, at least about 0.1 degrees Celsius, at least about 1 degree Celsius, at least about 5 degrees Celsius, at least about 10 degrees Celsius, or at least about 15 degrees Celsius hotter than the minimum temperature within the structural element and/or network of electrically conductive nanostructures.

In some embodiments, a single temperature determination may be sufficient to determine a mechanical characteristic of a structural element. For example, in one set of embodiments, a temperature can be measured at a single location on or within a structural element. In some cases, the temperature may indicate whether a defect is present at that location (e.g., if the temperature exceeds a pre-determined ceiling value, or if the temperature is lower than a pre-determined floor value).

In some cases, the methods described herein may include determining a second temperature. The determination of a mechanical characteristic of a structural element can be based, in some such cases, by comparing the values of the first and second temperatures. In one set of embodiments, a first temperature can be measured at a first location on or within a structural element, and a second temperature can be measured at a second, different location on or within the structural element. In some cases, a first temperature can be measured at a first time and a second temperature can be measured at a second, later time (e.g., at a different location or at the same location on or within the structural element).

In some cases, the first and second temperatures may have different values which may indicate a mechanical characteristic at one of the two locations. For example, if the first temperature is substantially lower than the second temperature, the first location may correspond to the interior of a discontinuity (e.g., a crack) while the second temperature may correspond to the bulk of the structural element. In some such cases, the second, higher temperature may correspond to the edge of a discontinuity or a region on the periphery of a discontinuity while the first, lower temperature may correspond to the bulk of the structural element. In some cases, the first and second temperatures may have substantially similar values which may indicate a substantially similar mechanical characteristic (or lack thereof) at each of the two locations.

In some embodiments, three, four, five, or more temperatures can be measured. In some instances, a large number of temperatures can be measured. For example, in some cases, an array of temperatures can be measured simultaneously using, for example, an imaging device such as a thermographic camera (e.g., an infrared thermographic camera). In some embodiments, an array of temperature data (e.g., an image from a thermographic camera) can be used to determine one or more mechanical characteristics by analyzing temperature differences (e.g., temperature gradients, differences in temperature between two or more discontinuous locations, etc.) within a single array (e.g., image). Such methods can be useful, for example, in determining one or more characteristics of a structural element in a steady-state analysis. In some embodiments, an graphical array of temperature data can be used to determine one or more mechanical characteristics by analyzing temperature differences (e.g., temperature gradients, differences in temperature between two or more discontinuous locations, etc.) within multiple arrays. For example, in some embodiments, multiple images of the same structural element taken at different times can be analyzed, which can be useful, for example, in performing a time-dependent determination of one or more mechanical characteristics of a single structural element. In some cases, two or more images of two or more structural elements (taken at the same or different times and/or locations) can be analyzed, which can be useful, for example, in determining one or more structural features of a first structural element relative to those observed in another (or more) structural elements. In some embodiments, determining a temperature includes determining a continuous gradient of temperatures across a line or surface on or within the structural element. For example, in some cases, determination of a temperature can include analysis of a single thermal image obtained, for example, from a thermographic camera. In some cases, determining a temperature can include determining a discontinuous gradient of temperatures across a line or surface on or within the structural element. For example, in some cases, determination of a temperature can include analysis of multiple thermal images of discontinuous parts of a structural element obtained, for example, from a thermographic camera.

In some embodiments, one or more temperatures can be determined during the application of an electrical current. One or more temperatures can also be determined, in some embodiments, after the application of the electrical current has been discontinued. Some such embodiments can allow one to determine one or more temperatures and/or mechanical characteristics of the structural element (and/or network of electrically conductive nanostructures) as its temperature decreases (e.g., via exposure to the ambient atmosphere, via exposure to a coolant source such as a stream of cold fluid, etc.).

A temperature of the structural element can be determined, in some instances, prior to first use of the structural element, after first use of the structural element, or both. For example, in some embodiments, a first temperature can be determined prior to first use, and a second temperature can be determined after use, for example, to determine one or more mechanical characteristics resulting from use of the article. As used herein, "prior to first use of the structural element" means a time or times before the structural element is first used by an intended user after commercial sale.

The systems, articles and methods described herein can include electrically conductive nanostructures arranged in a variety of ways. In some cases, such as the set of embodiments illustrated in FIGS. 1A-1B, a structural element can include a network of electrically conductive nanostructures that is distributed within the bulk of the structural element. For example, in some cases, the structural element can comprise a composite material including a plurality of nanostructures arranged within a primary structural material that can serve, for example, as a support material (e.g., monomers, polymers (e.g., epoxies, thermosets, thermoplastics, etc.), fibers, woven fabrics, ceramics, etc.). Systems and methods for fabricating such materials are described in detail below. In some cases, the network of electrically conductive nanostructures can be distributed substantially evenly throughout the bulk of the structural element.

Figure 3A:
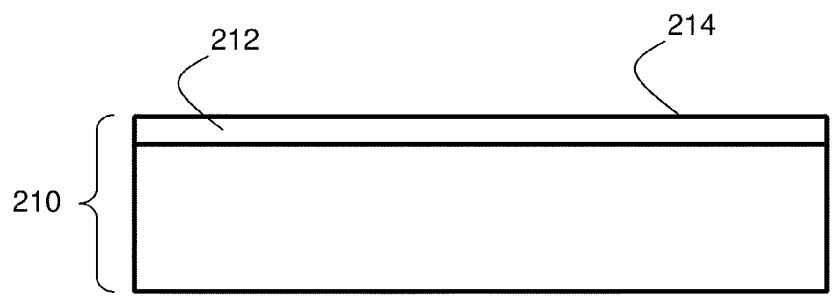
FIGS. 3A-3D include exemplary schematic diagrams of structural elements including layers.
Figure 3B:
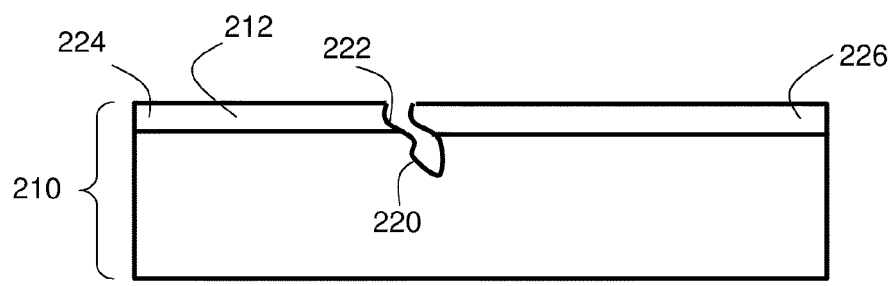
Figure 3C:
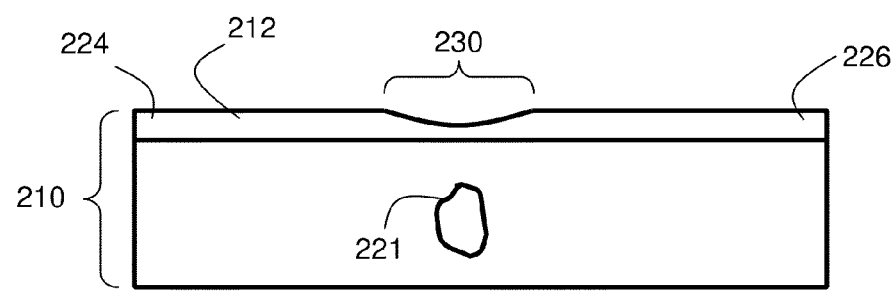

In some embodiments, a network of electrically conductive nanostructures can be located within a layer of the structural element. FIGS. 3A-3C illustrate one set of some such embodiments. In some embodiments, at least a portion of the layer in which the electrically conductive nanostructures are located defines an external surface of the structural element. In some cases, a majority of the layer in which the nanostructures are located defines an external surface of the structural element, and in some instances, substantially all of the layer a majority of the layer in which the nanostructures are located defines an external surface of the structural element. For example, FIG. 3A includes a cross-sectional schematic illustration of structural element 210 including a layer 212 within which electrically conductive nanostructures are distributed. In FIG. 3A, substantially all of layer 212 defines an external surface 214 of the structural element.

Defects or other mechanical characteristics of the structural element can be detected, in some embodiments, by passing an electrical current through a layer in which electrically conductive nanostructures are contained (e.g., layer 212 in FIG. 3A), and determining a temperature. Such embodiments can be useful, for example, when performing non-destructive structural health monitoring on a non-electrically-conductive structural article in which electrically conductive nanostructures are substantially absent within its bulk.

For example, in the set of embodiments illustrated in FIG. 3B, structural element 210 includes a crack 220 that has propagated through the structural element to produce a corresponding crack 222 in electrically conductive layer 212. In some cases, structural element 210 may not be electrically conductive. In addition, electrically conductive nanostructures may be substantially absent from structural element 210. In some cases, a layer of the structural element (e.g., electrically conductive layer 212, which can contain electrically conductive nanostructures) can be used to determine a mechanical characteristic of structural element 210. For example, when a voltage is applied across locations 224 and 226 of electrically conductive layer 212, a temperature (e.g., within the crack in the layer, along the edge of the crack, in a peripheral region adjacent the crack, etc.) can be determined that is indicative of crack 222 and, therefore, crack 220.

As another example, the structural element in the set of embodiments illustrated in FIG. 3C includes discontinuity 221 within the interior of the structural element. Discontinuity 221 can produce, in some instances, a strain on electrically conductive layer 212, which may produce, for example, a region with a relatively thin cross sectional area (e.g., region 230 in FIG. 3C). Upon applying a voltage across locations 224 and 226 of the layer, a temperature (e.g., within region 230) can be determined (e.g., a higher temperature due to an increased resistance to electrical conductivity) that is indicative of discontinuity 221. In some cases, discontinuity 221 may change the heat conduction in the bulk of structural element 210, which may project as a difference in layer 212.

In some cases, a layer (e.g., a film) including a network of electrically conductive nanostructures can be applied to the surface of a structural element (e.g., a component of an airplane, automobile, building, bridge, etc.). Optionally, an electrical current can be passed through the network of electrically conductive nanostructures within the layer, and one or more temperatures of the layer can be determined, for example, to establish a reference temperature for comparison to later temperature measurements. The structural element can then be used while the layer is deposited on the structure. During use, mechanical characteristics (e.g., cracks, dislocations, plastic deformations, etc.) that develop within the structural element may be transferred to the layer such that the layer and/or the network of conductive nanostructures within the layer is altered (e.g., via any of the pathways discussed above in relation to FIGS. 1A-1B). During and/or after use, an electrical current can be passed through the network of electrically conductive nanostructures within the layer, and one or more temperatures can be determined. A mechanical characteristic of the structural element can then be determined based at least in part on the one or more temperatures determined during and/or after use of the article.

Figure 3D:
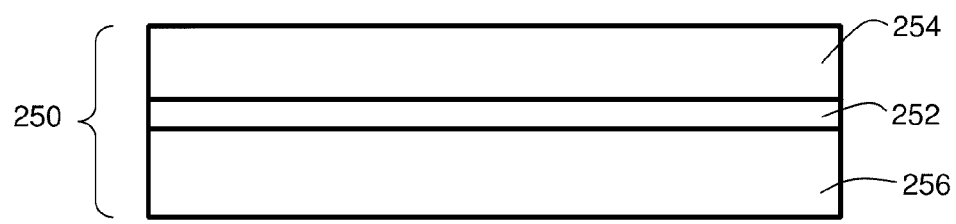

In some embodiments, the network of electrically conductive nanostructures can be contained within a layer, and at least a portion, at least a majority, or substantially all of the layer can be located within other materials (which might be substantially free of electrically conductive nanostructures) that define the outer boundaries of the structural element. In some cases, the layer can define an internal surface (e.g., an interface between two different materials, an interface between two similar materials, etc.) of the structural element. As a specific example, an interior surface can be formed between facesheets of a core material such as Al honeycomb in a sandwich panel. In some cases, the layer containing the network of electrically conductive nanostructures can be one of a plurality of layers within the structural element (e.g., in the case of a multi-layer laminated article). For example, in the set of embodiments illustrated in FIG. 3D, structural element 250 includes layer 252 which contains a network of electrically conductive nanostructures. In this set of embodiments, layer 252 is sandwiched between layers 254 and 256 of structural element 250. In some cases, layer 252 can comprise a primary structural material that is different from the primary structural material of layer 254 and/or layer 256. For example, in some cases, layer 252 may contain a polymeric primary structural material, while layer 254 and/or 256 may contain a ceramic primary structural material. In some embodiments, layer 252 can comprise a primary structural material that is similar to the primary structural material of layer 254 and/or layer 256. For example, in some cases, layer 252 and one or more other layers may comprise a similar polymeric material between which one or more interfaces exists (e.g., due to successive depositions of similar materials). In some cases, the network of electrically conductive nanostructures can be contained within a layer-like region within the bulk of a primary structural material of the structural element.

Figure 4:
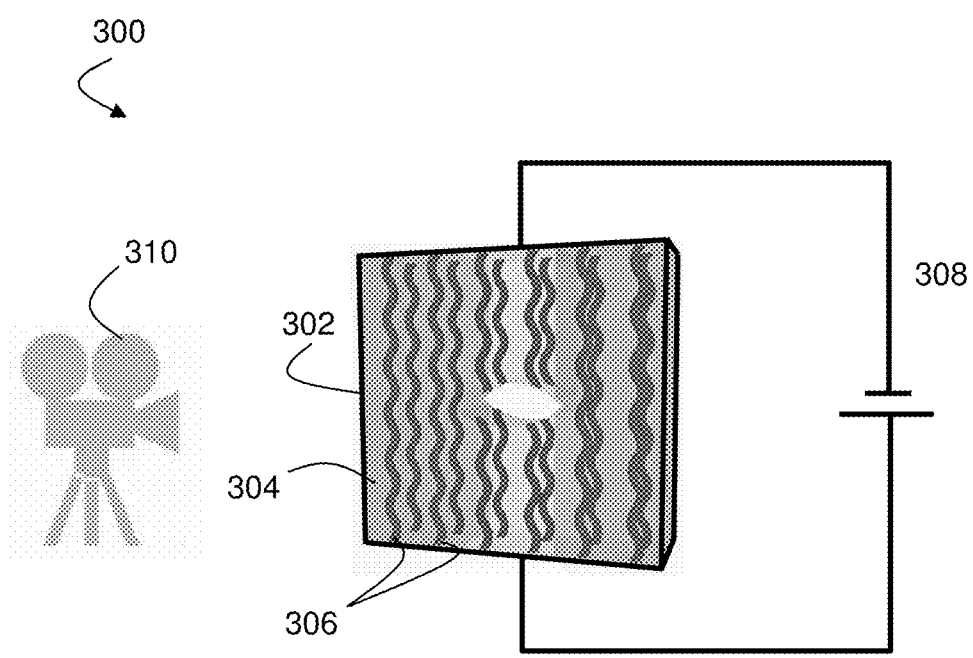
FIG. 4 includes a schematic diagram of a system for determining one or more mechanical characteristics of a structural article, according to one set of embodiments.

In one set of embodiments, a system is described. An exemplary system for determining a characteristic of a structural element is outlined in the schematic illustration of FIG. 4. In this set of embodiments, system 300 includes a structural element 302 comprising a primary structural material 304 and a network of electrically conductive nanostructures 306. In addition, the system can comprise an electrical circuit comprising the network (e.g., 308 in FIG. 4). The system can also comprise a sensor associated with the electrical circuit, constructed and arranged to determine a first temperature of the structural element. For example, the set of embodiments illustrated in FIG. 4 includes a thermographic camera 310 that can be used to determine a temperature of structural element 302. Other suitable sensors that may be used include, but are not limited to, thermocouples (e.g., a single thermocouple, a plurality of thermocouples), thermal indicator films (e.g., comprising temperature sensitive paint such as thermochromic paint, a liquid crystal slurry, and the like), piezoresistive temperature sensors, piezoelectric temperature sensors, thermoelectric sensors, and the like.

In some embodiments, the systems and methods described herein may be capable of determining a relatively small mechanical characteristic of a structural element. For example, in some embodiments, a mechanical characteristic with a maximum cross-sectional dimension of less than about 100 mm, less than about 10 mm, less than about 1 mm, less than about 0.1 mm, between about 0.01 mm and about 100 mm, between about 0.01 mm and about 10 mm, between about 0.01 mm and about 1 mm, between about 0.01 mm and about 0.1 mm, between about 0.1 mm and about 100 mm, between about 0.1 mm and about 10 mm, or between about 0.1 mm and about 1 mm can be determined.

A mechanical characteristic of a structural element can be determined, in some embodiments, by applying a relatively low amount of power to pass the electrical current through the network of electrically conductive nanostructures. In some cases, passing the electrical current through the network of electrically conductive nanostructures can comprise application of a power of less than about 100 Watts, less than about 10 Watts, less than about 1 Watt, less than about 0.1 Watts, between about 0.01 Watts and about 100 Watts, between about 0.01 Watts and about 10 Watts, between about 0.01 Watts and about 1 Watt, between about 0.1 Watts and about 100 Watts, between about 0.1 Watts and about 10 Watts, or between about 0.1 Watts and about 1 Watt.

In some embodiments, a mechanical characteristic of a structural element can be determined by establishing a relatively low voltage across the network of electrically conductive nanostructures. For example, in some cases, passing an electrical current through the network of electrically conductive nanostructures can comprise establishing a voltage difference of less than about 100 Volts, less than about 50 Volts, less than about 10 Volts, less than about 1 Volt, less than about 0.1 Volts, less than about 0.01 Volts, between about 0.001 Volts and about 100 Volts, between about 0.001 Volts and about 50 Volts, between about 0.001 Volts and about 10 Volts, between about 0.001 Volts and about 1 Volts, between about 0.01 Volts and about 100 Volts, between about 0.01 Volts and about 50 Volts, between about 0.01 Volts and about 10 Volts, between about 0.01 Volts and about 1 Volts, between about 0.1 Volts and about 100 Volts, between about 0.1 Volts and about 50 Volts, between about 0.1 Volts and about 10 Volts, between about 0.1 Volts and about 1 Volts, between about 1 Volt and about 100 Volts, between about 1 Volt and about 50 Volts, or between about 1 Volt and about 10 Volts.

In some instances, the application of a power and/or voltage (e.g., within any of the ranges noted herein) can elevate the temperature of at least a portion of the structural element and/or network of electrically conductive nanostructures, relative to the ambient environment, by at least about 0.01 degrees Celsius, at least about 0.1 degrees Celsius, at least about 1 degree Celsius, at least about 5 degrees Celsius, at least about 10 degrees Celsius, at least about 15 degrees Celsius, or more. In some cases, the application of a power and/or voltage (e.g., within any of the ranges noted herein) can produce a maximum temperature within the structural element and/or network of electrically conductive nanostructures at least about 0.01 degrees Celsius, at least about 0.1 degrees Celsius, at least about 1 degree Celsius, at least about 5 degrees Celsius, at least about 10 degrees Celsius, or at least about 15 degrees Celsius hotter than the minimum temperature within the structural element and/or network of electrically conductive nanostructures.

The electrically conductive nanostructures can be elongated structures, in some cases. For example, in some embodiments, an electrically conductive nanostructure can have a diameter on the order of nanometers and a length on the order of microns to millimeters or more. In some instances, the electrically conductive nanostructures can have an aspect ratio greater than 3, 10, 100, 1000, 10,000, or greater. In such cases, the nanostructures may have a long axis. The term "long axis" is used to refer to the imaginary line drawn parallel to the longest length of the nanostructure and intersecting the geometric center of the nanostructure.

The long axes of the plurality of nanostructures within the structural element can be, in some cases, substantially aligned. For example, in one set of embodiments, the structural article can include a plurality of nanostructures wherein at least about 50%, at least about 75%, at least about 90%, at least about 95%, or at least about 99% of the long axes of the nanostructures within the structural element (or a portion thereof) are substantially aligned. In addition, in some embodiments, at least about 50%, at least about 75%, at least about 90%, at least about 95%, or at least about 99% of the nanostructures are continuous from end to end of the structural element. In some cases, the alignment of the long axes of nanostructures may provide the ability to tailor one or more anisotropic properties of a material, including mechanical, thermal, electrical, and/or other properties. As specific examples, the nanostructures may be arranged to enhance the intralaminar interactions of components within the structural element, to enhance the interlaminar interactions of two substrates or plies within a structural element (e.g., a composite structure), or to mechanically strengthen or otherwise enhance the binding between the two substrates within a structural element, among other functions. In some cases a structural element may exhibit a higher mechanical strength and/or toughness when compared to an essentially identical structural element lacking the plurality of substantially-aligned nanostructures, under essentially identical conditions. In some cases, a structural element may exhibit a higher thermal and/or electrical conductivity when compared to an essentially identical structural element lacking the plurality of substantially-aligned nanostructures, under essentially identical conditions. In some cases, the electrical conductivity, thermal conductivity, and/or other properties (e.g., electromagnetic properties, specific heat, etc.) of the structural element may be anisotropic.

In some cases, the electrically conductive nanostructures can be dispersed substantially uniformly within the primary structural material and/or a layer (e.g., a film) containing a plurality of electrically conductive nanostructures. For example, in some cases, the nanostructures may be dispersed substantially uniformly within at least 10% of a primary structural material or a layer (e.g., film), or, in some cases, at least 20%, 30%, 40%, 50%, 60%, 70%, 80%, 90%, 95%, or 100% of a primary structural material or a layer (e.g., film). As used herein, "dispersed uniformly within at least X%" of a volume refers to the substantially uniform arrangement of nanostructures within at least X% of the volume. The ability to arrange nanostructures substantially uniformly throughout a primary structural material and/or a layer (e.g., film) comprising a plurality of electrically conductive nanostructures can allow for relatively consistent electrical conductivity, thermal conductivity, and/or mechanical properties (e.g., strength, modulus, etc.) within the primary structural material and/or the layer (e.g., film).

In some embodiments, the nanostructures can be arranged such that they penetrate at least one surface formed between two articles that are joined to each other (e.g., to form a layered composite). For example, in some cases, two layers of material can be joined to form a layered composite, and the nanostructures can be arranged at the interface of the joined layers such that, for at least some of the nanostructures, a first portion of the nanostructure is positioned within the first layer and a second portion of the nanostructure is positioned within the second layer. In this arrangement, the length of the nanostructure can extend across the interface formed between the first and second layers of material, which can reinforce the interface between the first and second layers, in some embodiments.

The electrically conductive nanostructures can also be distributed according to pre-determined patterns, in some instances. For example, arranging the nanostructures in pre-determined patterns (e.g., non-uniformly within the primary structural material of the structural article) can allow spatial tailoring of electrical conductivity, thermal conductivity, and/or mechanical properties (e.g., strength, modulus, etc.) within the primary structural material and/or a layer (e.g., a film). Spatial tailoring may be useful in accentuating sensitivity to defects of interest, such as in interfaces where structures are bonded together (e.g., in composites). In some cases, the electrically conductive nanostructures may be present in relatively high concentrations within a region of particular interest (e.g., a corner, a region around a bolt hole, a bond line at an interface, etc.). In some embodiments, the nanostructures can be arranged such that a pre-determined temperature distribution is achieved upon passing an electrical current through the structural element. In some cases, the magnitude of the electrical current and/or voltage that is applied to the structural element can be chosen such that the desired temperature distribution is achieved.

In some embodiments, the nanostructures within the structural element may be closely spaced. For example, the average distance between adjacent nanostructures may be less than about 500 nm, less than about 200 nm, less than about 100 nm, less than about 80 nm, less than about 60 nm, less than about 40 nm, less than about 30 nm, less than about 20 nm, less than about 10 nm, less than about 5 nm, or smaller. In some cases, the nanostructure materials or the nanocomposites may comprise a high volume fraction of nanostructures. For example, the volume fraction of the nanostructures within the materials may be at least about 10%, at least about 20%, at least about 40%, at least about 60%, at least about 70%, at least about 75%, at least about 78%, or higher. In some embodiments, the volume fraction of the nanostructures (e.g., within a particular region of the structural element, within the entire volume of the structural element, etc.) can be selected such that a desired electrical resistance, temperature, or other property can be obtained upon applying a pre-determined voltage.

As described herein, the systems and methods described herein may involve use or addition of one or more primary structural materials. In some cases, the primary structural material and the network of electrically conductive nanostructures may form a composite material. For example, in some cases, the primary structural material may comprise a material (e.g., a monomer, a polymer, etc.) that is selected to uniformly "wet" the nanostructures and/or to bind one or more substrates.

In some embodiments, all of part of the primary structural material can have an electrical resistivity of at least about 100 Ohm m, at least about 1000 Ohm m, at least about $1\times10^4$ Ohm m, at least about $1\times10^6$ Ohm m, at least about $1\times10^8$ Ohm m, at least about $1\times10^{10}$ Ohm m, at least about $1\times10^{12}$ Ohm m, at least about $1\times10^{14}$ Ohm m, at least about $1\times10^{16}$ Ohm m, at least about $1\times10^{18}$ Ohm m, at least about $1\times10^{20}$ Ohm m, between about 100 Ohm m and about $1\times10^{30}$ Ohm m, between about 1000 Ohm m and about $1\times10^{30}$ Ohm m, between about $1\times10^4$ Ohm m and about $1\times10^{30}$ Ohm m, between about $1\times10^6$ Ohm m and about $1\times10^{30}$ Ohm m, between about $1\times10^8$ Ohm m and about $1\times10^{30}$ Ohm m, between about $1\times10^{10}$ Ohm m and about $1\times10^{30}$ Ohm m, between about $1\times10^{12}$ Ohm m and about $1\times10^{30}$ Ohm m, or between about $1\times10^{14}$ Ohm m and about $1\times10^{30}$ Ohm m, for example at 20° C. In some embodiments, the primary structural material can have an average electrical resistivity within any of the above ranges. Any of the layers of primary structural material described herein can include a material that has an electrical resistivity within the ranges outlined above. For example, in the set of embodiments illustrated in FIGS. 1A-1B, primary structural material 12 can have an electrical resistivity within any of the ranges outlined above. As another example, in the set of embodiments illustrated in FIG. 3D, the primary structural materials in layers 252, 254 and/or 256 can have an electrical resistivity within any of the ranges outlined above.

Polymer materials that may be suitable for use as primary structural materials can include any material compatible with nanostructures. In some cases, the polymer material may be selected to have a particular viscosity, such as 500,000 cPs or lower, 100,000 cPs or lower, 50,000 cPs or lower, 10,000 cPs or lower, 5,000 cPs or lower, 1,000 cPs or lower, 500 cPs or lower, 250 cPs or lower, or, 100 cPs or lower. In some embodiments, the polymer material may be selected to have a viscosity between 150-250 cPs. In some cases, the polymer material may be a thermoset or thermoplastic. In some cases, the polymer material may not be substantially electrically conductive, while in other cases, the polymer material may be substantially electrically conductive.

Examples of thermosets that may be suitable for use as primary structural materials include Microchem SU-8 (UV curing epoxy, grades from 2000.1 to 2100, and viscosities ranging from 3 cPs to 10,000 cPs), Buehler Epothin (low viscosity, ~150 cPs, room temperature curing epoxy), West Systems 206+109 Hardener (low viscosity, ~200 cPs, room temperature curing epoxy), Loctite Hysol 1C (20-min curing conductive epoxy, viscosity 200,000-500,000cPs), Hexcel RTM6 (resin transfer molding epoxy, viscosity during process ~10 cPs), Hexcel HexFlow VRM 34 (structural VARTM or vacuum assisted resin transfer molding epoxy, viscosity during process ~500 cPs). Examples of thermoplastic include polystyrene, or Microchem PMMA (UV curing thermoplastic, grades ranging from 10 cPs to ~1,000 cPs). In one embodiment, the polymer material may be PMMA, EpoThin, WestSystems EPON, RTM6, VRM34, 977-3, SU8, or Hysol1C.

Any suitable source and/or type of electrical current can be used in the systems and methods described herein. For example, direct current (DC), alternating current (AC), or combination of DC and AC can be used. Suitable sources of electrical current can include, but are not limited to, batteries (e.g., alkaline batteries, NiMH batteries, and the like), variable power supplies, or any other suitable source. One of ordinary skill in the art would be capable of selecting a suitable source and/or type of electrical current for a particular application.

In some cases, the nanostructures may be grown on a substrate. Nanostructures may be grown on a substrate using either a batch process or a continuous process. In one set of examples, the nanostructures may be synthesized by contacting a nanostructure precursor material with a catalyst material, for example, positioned on a surface of the growth substrate. In some embodiments, the nanostructure precursor material may be a nanotube precursor material and may comprise one or more fluids, such as a hydrocarbon gas, hydrogen, argon, nitrogen, combinations thereof, and the like. Those of ordinary skill in the art would be able to select the appropriate combination of nanotube precursor material, catalyst material, and set of conditions for the growth of a particular nanostructure. For example, carbon nanotubes may be synthesized by reaction of a $C_2H_4/H_2$ mixture with a catalyst material, such as nanoparticles of Fe arranged on an $Al_2O_3$ support. Examples of suitable nanostructure fabrication techniques are discussed in more detail in International Patent Application Serial No. PCT/US2007/011914, filed May 18, 2007, entitled "Continuous Process for the Production of Nanostructures Including Nanotubes," published as WO 2007/136755 on Nov. 29, 2007, which is incorporated herein by reference in its entirety.

In some embodiments (e.g., in which the nanostructures are grown on a substrate), nanostructures (e.g., elongated nanostructures) can be arranged (e.g., grown) such that they are substantially aligned. In some cases, the set of substantially aligned nanostructures may be oriented such that the long axes of the nanostructures are substantially non-parallel to the surface of the substrate (e.g., a growth substrate). In some cases, the long axes of the nanostructures are oriented in a substantially perpendicular direction with respect to the surface of the growth substrate, forming a nanostructure "forest." An advantageous feature of some embodiments of the invention may be that the alignment of nanostructures in the nanostructure "forest" may be substantially maintained, even upon subsequent processing (e.g., application of a force to the forest, transfer of the forest to other surfaces, and/or combining the forests with materials such as polymers, metals, ceramics, piezoelectric materials, piezomagnetic materials, carbon, and the like).

In some cases, the method may comprise the act of removing the nanostructures from the growth substrate. In some cases, the nanostructures may be covalently bonded to the substrate, and the removal step comprises breaking at least some of the covalent bonds. The act of removing may comprise transferring the nanostructures directly from the surface of the growth substrate to a surface of a receiving substrate. Removal of the nanostructures may comprise application of a mechanical tool, mechanical or ultrasonic vibration, a chemical reagent, heat, or other sources of external energy, to the nanostructures and/or the surface of the growth substrate. For example, a scraping ("doctor") or peeling blade, and/or other means such as an electric field may be used to initiate and continue delamination of the nanostructures from the substrate. In some cases, the nanostructures may be removed by application of compressed gas, for example. In some cases, the nanostructures may be removed (e.g., detached) and collected in bulk, without attaching the nanostructures to a receiving substrate, and the nanostructures may remain in their original or "as-grown" orientation and conformation (e.g., in an aligned "forest") following removal from the growth substrate.

In one set of embodiments, the attachment between the nanostructures and a substrate (e.g., via covalent bonding) may be altered by exposing the nanostructures and/or substrate to a chemical (e.g., a gas). Exposing the nanostructures and/or substrate to the chemical may, in some cases, substantially reduce the level of attachment between the nanostructures and the substrate. Examples of chemicals that are useful in reducing the level of attachment between the nanostructures and the substrate include, but are not limited to, hydrogen, oxygen, and air, among others. In some cases, elevated temperatures (e.g., temperatures greater than about 100° C.) may be used to expedite the detachment of nanostructures from the substrate. For example, nanostructures (e.g., carbon nanotubes) may be grown on a growth substrate and subsequently exposed to hydrogen gas while they remain in the processing chamber. Exposing the nanostructures to hydrogen may, in some cases, result in the delamination of the nanostructures from the growth substrate. In some embodiments, exposing the nanostructures to hydrogen may not result in the complete delamination of the plurality of nanostructures, but may, for example, result in the breaking of a large enough fraction of the bonds such that the force required to remove the plurality of nanostructures is reduced by at least about 50%, at least about 70%, at least about 90%, at least about 95%, at least about 99%, or more.

As described above, some embodiments may make use of a growth substrate on which nanostructures are formed. Growth substrates described herein may be any material capable of supporting nanostructures and/or catalyst materials as described herein. The growth substrate may be selected to be inert to and/or stable under sets of conditions used in a particular process, such as nanostructure growth conditions, nanostructure removal conditions, and the like. In some cases, the growth substrate comprises a substantially flat surface. In some cases, the growth substrate comprises a substantially nonplanar surface. For example, the growth substrate may comprise a cylindrical surface. Examples of growth substrates suitable for use in the systems and methods described herein include, but are not limited to, prepregs, polymer resins, dry weaves and tows, inorganic materials such as carbon (e.g., graphite), metals, alloys, intermetallics, metal oxides, metal nitrides, ceramics, and the like. In some cases, the growth substrate may be a fiber, tow of fibers, a weave, and the like. Growth substrates may, in some cases, further comprise a conducting material, such as conductive fibers, weaves, or nanostructures.

In some cases, the growth substrate may be incorporated into a structural element. For example, in some cases, the growth substrate may include a plurality of fibers on which nanostructures are grown. After growth of the nanostructures, a primary structural material (e.g., a monomer, a polymer, a ceramic, etc.), which can, in some cases, include a non-electrically conductive material, may be added to the plurality of fibers and the nanostructures to form a composite structural element.

In some embodiments, the substrates used herein are substantially transparent to electromagnetic radiation. For example, in some cases, the substrate may be substantially transparent to visible light, ultraviolet radiation, or infrared radiation.

In some cases, the substrates as described herein may be prepregs, that is, a polymer material (e.g., thermoset or thermoplastic polymer) containing embedded, aligned, and/or interlaced (e.g., woven or braided) fibers such as carbon fibers. As used herein, the term "prepreg" refers to one or more layers of thermoset or thermoplastic resin containing embedded fibers, for example fibers of carbon, glass, silicon carbide, and the like. In some embodiments, thermoset materials include epoxy, rubber strengthened epoxy, BMI, PMK-15, polyesters, vinylesters, and the like, and preferred thermoplastic materials include polyamides, polyimides, polyarylene sulfide, polyetherimide, polyesterimides polyarylenes polysulfones polyethersulfones polyphenylene sulfide, polyetherimide, polypropylene, polyolefins, polyketones, polyetherketones, polyetherketoneketone, polyetheretherketones, polyester, and analogs and mixtures thereof. Typically, a prepreg can include fibers that are aligned and/or interlaced (woven or braided) and the prepregs can be arranged such the fibers of many layers are not aligned with fibers of other layers, the arrangement being dictated by directional stiffness requirements of the article to be formed by the method. In some embodiments, the fibers cannot be stretched appreciably longitudinally, thus each layer cannot be stretched appreciably in the direction along which its fibers are arranged. Exemplary prepregs include TORLON thermoplastic laminate, PEEK (polyether etherketone, Imperial Chemical Industries, PLC, England), PEKK (polyetherketone ketone, DuPont) thermoplastic, T800H/3900-2 thermoset from Toray (Japan), and AS4/3501-6 thermoset from Hercules (Magna, Utah).

As described above, a variety of nanostructures can be used in association with the nanosensors described herein. In some embodiments, the nanostructures include a fused network of atomic rings, the atomic rings comprising a plurality of double bonds. In some embodiments, nanostructures described herein can have at least one cross-sectional dimension between two opposed boundaries of less than about 500 nm, less than about 250 nm, less than about 100 nm, less than about 75 nm, less than about 50 nm, less than about 25 nm, less than about 10 nm, or, in some cases, less than about 1 nm.

In some embodiments, carbon-based nanostructures are described. As used herein, a "carbon-based nanostructure" comprises a fused network of aromatic rings wherein the nanostructure comprises primarily carbon atoms. In some instances, the nanostructures have a cylindrical, pseudo-cylindrical, or horn shape. A carbon-based nanostructure can comprises a fused network of at least about 10, at least about 50, at least about 100, at least about 1000, at least about 10,000, or, in some cases, at least about 100,000 aromatic rings. Carbon-based nanostructures may be substantially planar or substantially non-planar, or may comprise a planar or non-planar portion. Carbon-based nanostructures may optionally comprise a border at which the fused network terminates. For example, a sheet of graphene comprises a planar carbon-containing molecule comprising a border at which the fused network terminates, while a carbon nanotube comprises a nonplanar carbon-based nanostructure with borders at either end. In some cases, the border may be substituted with hydrogen atoms. In some cases, the border may be substituted with groups comprising oxygen atoms (e.g., hydroxyl).

In some embodiments, the nanostructures described herein may comprise nanotubes. As used herein, the term "nanotube" is given its ordinary meaning in the art and refers to a substantially cylindrical molecule or nanostructure comprising a fused network of primarily six-membered rings (e.g., six-membered aromatic rings). In some cases, nanotubes may resemble a sheet of graphite formed into a seamless cylindrical structure. It should be understood that the nanotube may also comprise rings or lattice structures other than six-membered rings. Typically, at least one end of the nanotube may be capped, i.e., with a curved or nonplanar aromatic group. Nanotubes may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may comprise a carbon nanotube. The term "carbon nanotube" refers to nanotubes comprising primarily carbon atoms. Examples of carbon nanotubes include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, the carbon nanotube is a single-walled carbon nanotube. In some embodiments, the single-walled carbon nanotubes can be metallic single-walled carbon nanotubes. In some embodiments, the single-walled carbon nanotubes can be semi-conductive single-walled carbon nanotubes. In some cases, the carbon nanotube is a multi-walled carbon nanotube (e.g., a double-walled carbon nanotube).

In some instances, the nanostructures described herein (e.g., at least a portion, or substantially all, of the electrically conductive nanostructures within the structural element) can be nanoparticles. Generally, the term "nanoparticle" is used to refer to any particle having a maximum cross-sectional dimension of less than about 1 micron. In some embodiments, a nanoparticle within the structural element may have a maximum cross-sectional dimension of less than about 500 nm, less than about 250 nm, less than about 100 nm, less than about 10 nm, less than about 5 nm, less than about 3 nm, less than about 2 nm, less than about 1 nm, between about 0.3 and about 10 nm, between about 10 nm and about 100 nm, or between about 100 nm and about 1 micron. In some cases, the average maximum cross-sectional dimension of substantially all of the nanoparticles of the same type (e.g., substantially all of the metal nanoparticles, substantially all of the carbon black nanoparticles, etc.) can be less than about 500 nm, less than about 100 nm, less than about 10 nm, less than about 5 nm, less than about 3 nm, less than about 2 nm, less than about 1 nm, between about 0.3 and about 10 nm, between about 10 nm and about 100 nm, or between about 100 nm and about 1 micron. As used herein, the "maximum cross-sectional dimension" (e.g., of a nanostructure, of a structural element, etc.) refers to the largest distance between two opposed boundaries of an individual structure that may be measured. The "average maximum cross-sectional dimension" of a plurality of structures refers to the number average.

As mentioned, the structural element can comprise a network of electrically conductive nanostructures. In some embodiments, all of part of the nanostructures within the structural element can have an electrical resistivity of less than about 0.1 Ohm m, less than about 0.01 Ohm m, less than about 0.001 Ohm m, less than about $1\times10^{-4}$ Ohm m, less than about $1\times10^{-6}$ Ohm m, less than about $1\times10^{-8}$ Ohm m, less than about $1\times10^{-10}$ Ohm m, less than about $1\times10^{-12}$ Ohm m, less than about $1\times10^{-14}$ Ohm m, less than about $1\times10^{-16}$ Ohm m, less than about $1\times10^{-18}$ Ohm m, less than about $1\times10^{-20}$ Ohm m, between about $1\times10^{-30}$ Ohm m and about 1 Ohm m, between about $1\times10^{-30}$ Ohm m and about 0.1 Ohm m, between about $1\times10^{-30}$ Ohm m and about 0.01 Ohm m, between about $1\times10^{-30}$ Ohm m and about 0.001 Ohm m. between about $1\times10^{-30}$ Ohm m and about $1\times10^{-4}$ Ohm m, between about $1\times10^{-30}$ Ohm m and about $1\times10^{-6}$ Ohm m, between about $1\times10^{-30}$ Ohm m and about $1\times10^{-8}$ Ohm m, between about $1\times10^{-30}$ Ohm m and about $1\times10^{-10}$ Ohm m, between about $1\times10^{-30}$ Ohm m and about $1\times10^{-12}$ Ohm m, or between about $1\times10^{-30}$ Ohm m and about $1\times10^{-14}$ Ohm m, for example at 20° C. In some embodiments, the average electrical resistivity of the nanostructures within the structural element can fall within any of the above ranges.

The articles, systems, and methods described herein may be combined with those described in International Patent Application Serial No. PCT/US2007/011914, filed May 18, 2007, entitled "Continuous Process for the Production of Nanostructures Including Nanotubes," published as WO 2007/136755 on Nov. 29, 2007; International Patent Application Serial No. PCT/US07/11913, filed May 18, 2007, entitled "Nanostructure-reinforced Composite Articles and Methods," published as WO 2008/054541 on May 8, 2008; International Patent Application Serial No. PCT/US2008/009996, filed Aug. 22, 2008, entitled "Nanostructure-reinforced Composite Articles and Methods," published as WO 2009/029218 on Mar. 5, 2009; U.S. Pat. No. 7,537,825, issued on May 26, 2009, entitled "Nano-Engineered Material Architectures: Ultra-Tough Hybrid Nanocomposite System;"

U.S. patent application Ser. No. 11/895,621, filed Aug. 24, 2007, entitled "Nanostructure-Reinforced Composite Articles," published as U.S. Patent Application Publication No. 2008/0075954 on Mar. 27, 2008; U.S. Provisional Patent Application 61/114,967, filed Nov. 14, 2008, entitled "Controlled-Orientation Films and Nanocomposites Including Nanotubes or Other Nanostructures;" U.S. patent application Ser. No. 12/630,289, filed Dec. 3, 2009, entitled "Multifunctional Composites Based on Coated Nanostructures," published as U.S. Patent Application Publication No. 2010/0255303 on Oct. 7, 2010; U.S. patent application Ser. No. 12/618,203, filed Nov. 13, 2009, entitled "Controlled-Orientation Films and Nanocomposites Including Nanotubes or Other Nanostructures," published as U.S. Patent Application Publication No. 2010/0196695 on Aug. 5, 2010; and U.S. Provisional Patent Application 61/230,267, filed Jul. 31, 2009, entitled "Systems and Methods Related to the Formation of Carbon-Based Nanostructures;" each of which is incorporated herein by reference in its entirety for all purposes.

The following documents are incorporated herein by reference in their entirety for all purposes: U.S. Provisional Patent Application Ser. No. 61/259,925, filed Nov. 10, 2009, and entitled "Systems and Methods Structural Sensing" and U.S. Provisional Patent Application Ser. No. 61/262,864, filed Nov. 19, 2009, and entitled "Systems and Methods for Structural Sensing." All other patents, patent applications, and documents cited herein are also hereby incorporated by reference in their entirety for all purposes.

EXAMPLES

The following examples are intended to illustrate certain embodiments of the present invention, but do not exemplify the full scope of the invention.

Example 1

This example describes the determination of one or more mechanical characteristics in structural elements via resistive heating. In this example, a differential voltage was applied to a network of carbon nanotubes (CNTs). Defects within the network of CNTs produced a change in the local resistivity, and therefore in temperature, which was measured using a thermal camera.

In this example, a vertically-aligned CNT forest was grown on a silicon wafer by placing the wafer in an atmospheric pressure quartz tube furnace (Lindberg). In order to grow CNTs, a Chemical Vapor Deposition process was used, flowing He, $C_2H_4$ and $H_2$ during the different growth steps. The growth temperature was 650° C., as measured by thermocouples in the tube furnace. Aligned MWCNTs were grown uniformly on the surface of the silicon wafer, to produce a 6 cm×4 cm (VACNT) forest. The CNTs appeared to be distributed uniformly over the silicon wafer, with a few clear spots observable with the naked eye (as indicated by white dots and small regions in FIG. 5A).

Figure 5A:
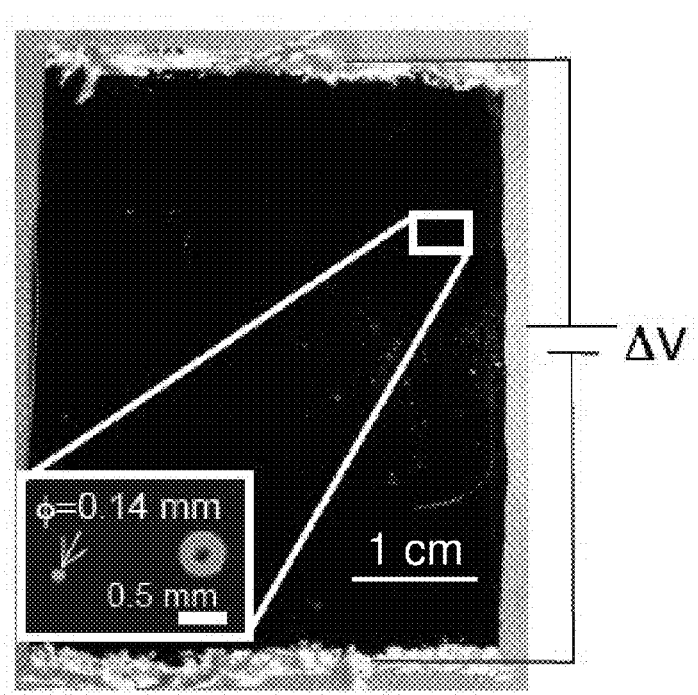
FIGS. 5A-5B include (A) a photograph and (B) a thermograph of a forest of aligned electrically conductive nanostructures, according to one set of embodiments.

A silver paste contact was painted on each side of the as-grown VACNT forest, as shown in FIG. 5A. Wires were attached to the paste before it was cured. A DC power supply was applied to the system to produce Joule effect heating. The surface was heated by applying 0.06 A and 20 V DC over 1 min in order to stabilize the thermal distribution.

Figure 5B:
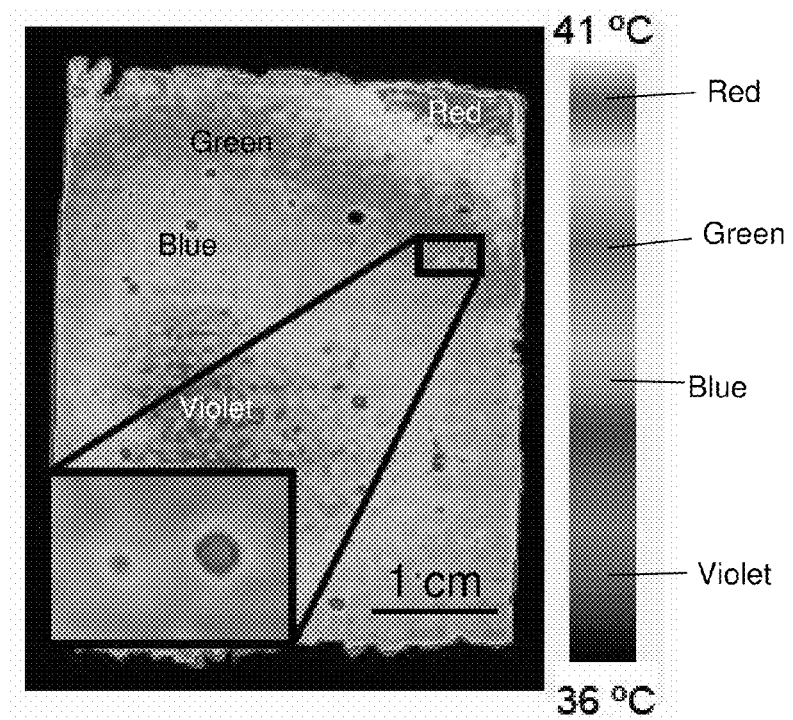

Thermal images were taken with a tripod-mounted thermal camera (PCE-TC 3, PCE group) every 30 seconds. Temperature was recorded using a 160 pixel×120 pixel array, with a temperature range of −10 to 250° C. and a resolution of 0.15° C. Samples were measured from a minimum measuring distance of 30 cm. This applied voltage resulted in a low temperature appearing on the surface of the forest, as shown in FIG. 5B. The thermal camera was capable of detecting non-CNT zones of under 0.14 mm in diameter. Electrical and thermal conductivity was produced in the direction perpendicular to the CNTs. Not wishing to be bound by any theory, this may have occurred due to entanglement of the CNTs. The CNT forest was observed under an optical microscope, and it was found that the low temperature regions corresponded to the zones where the surface of the silicon wafer could be seen due to the absence of CNT growth.

Similar experiments were performed using fuzzy fiber (FF) composite samples. The fuzzy fiber samples included alumina cloths in which CNTs were grown around the alumina fibers such that the CNTs were embedded in the cloth. To produce the FF alumina cloths, a high temperature alumina cloth (900 g/m², about 1 mm thick; 0°/90° satin-weave; McMaster-Carr) was dipped in a 50 mM solution of Fe $(NO_3)_3 \cdot 9H_2O$ in isopropanol. Once the solvent was evaporated, the cloth was placed in an atmospheric pressure quartz tube furnace (Lindberg). In order to grow CNTs, the Chemical Vapor Deposition process outlined above was used (i.e., flowing He, $C_2H_4$ and $H_2$ during the different growth steps at a growth temperature of 650° C.). Aligned 20 micron average length MWCNTs grew uniformly around each fiber in a "Mohawk" morphology as was observed by SEM characterization. Silver paste electrodes were attached to each end of the sample. 20 Volts (at 0.06 Amps) were applied to the sample, and a thermograph was taken. For the fuzzy fiber samples, no cold spots were observed as the cloth was substantially filled by inter- and intra-tow CNTs.

Example 2

Figure 6A:
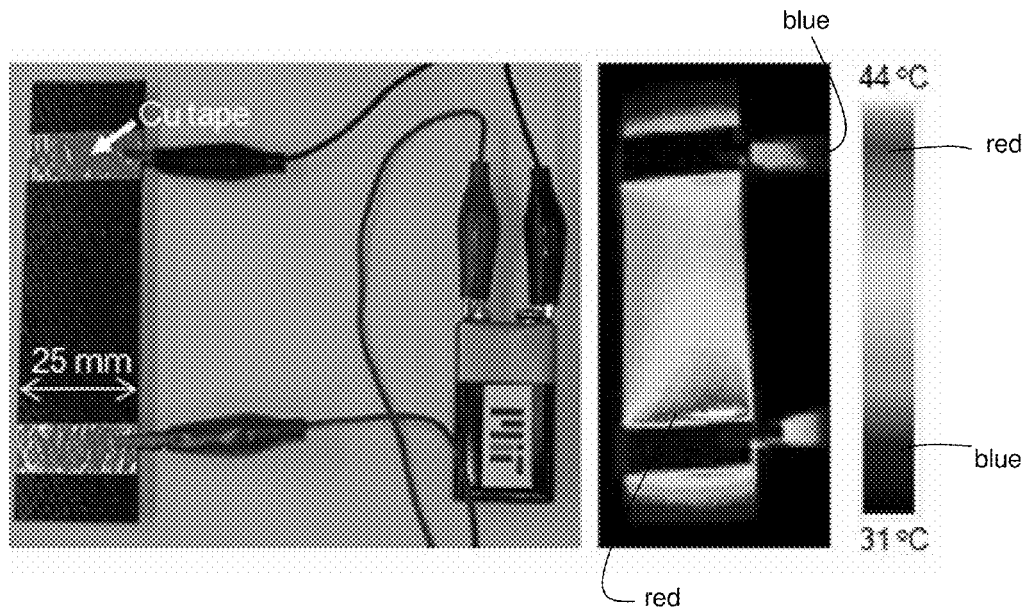
FIGS. 6A-6B include (A) a photograph of a structural element and (B) a plot of electrical resistance and temperature change as a function of power, according to one set of embodiments.

In this example, the effect of the amount of electrical power imparted to a composite sample on the system temperature was investigated. A nano-engineered composite specimen comprising 3 plies of fuzzy fiber alumina cloth and cured epoxy resin was heated varying the intensity of the power supply, as shown in FIG. 6A. The composite specimens were made using a hand lay-up method. A woven cloth comprising alumina fibers and CNTs (made using the techniques described in Example 1) was placed on a metal sheet coated with a Teflon film. A commercial epoxy (Resin 105 and Hardener 206 from West Systems Epoxy) was poured into a stack of 3 piles of the cloth. Capillarity forces allowed the aligned-CNTs wet substantially completely. The sample was sealed by a vacuum bag during the curing process to consolidate the laminate. The laminate had an alumina fiber volume fraction of about 50% alumina fiber volume fraction and a CNT volume fraction of about 2.6%. Once the laminate had cured, the specimens were trimmed.

Figure 6B:
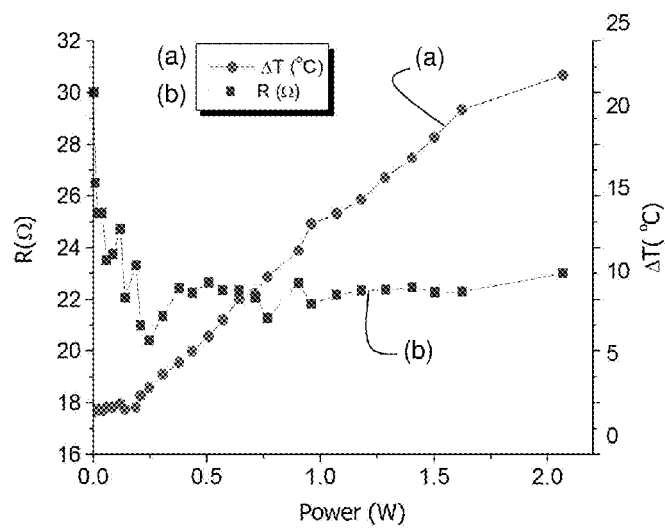

Conductive contacts were established with copper tape on each side of the specimen, as shown in FIG. 6A. The maximum temperature of the samples was recorded every 30 seconds in order to get a homogeneous thermal distribution on the sample. FIG. 6B includes a plot of resistance and temperature change as a function of the applied power for this set of experiments. As can be seen in FIG. 6B, at low powers (e.g., under 0.5 W), the resistance of the sample decreased until it reached a plateau, but the temperature increased only slightly. From 0.5 W to 1.75 W, the heating rate increased linearly at about 12.3° C./W. At powers over 1.75 W, the heating rate appeared to decrease. Not wishing to be bound by any theory, this might have been due to local resin degradation. At powers well over 1.75 W, sample temperatures of over 100° C. were observed, and smoke from the resin decomposition was detected. Notably, a temperature rise in the sample of about 20° C. was observed at about 2 W of applied power.

Example 3

This example describes an in situ tensile test in which the evolution of damage within a structure was observed. In this example, a nano-engineered composite specimen comprising 2 plies of fuzzy fiber alumina cloth and epoxy resin was used. The methods for producing the composite were similar to those described in Example 2. For the composite used in this example, a hole was drilled in the center of the composite (as shown in FIG. 7A) using a diamond grit core drill.

Figure 7A:
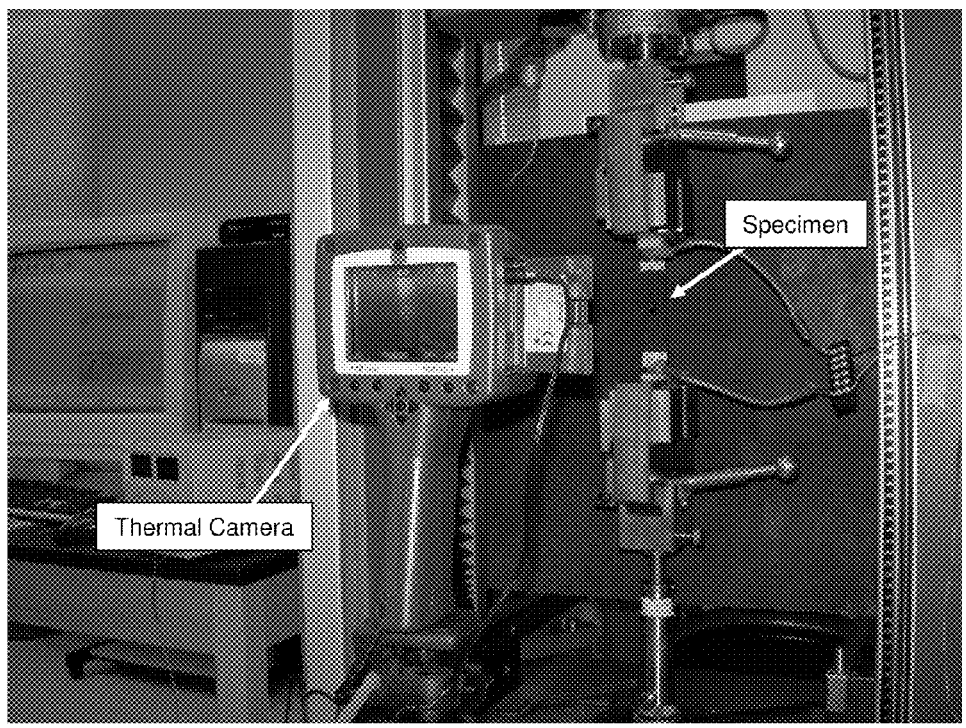
FIGS. 7A-7B include (A) a photograph of an exemplary system for determining a characteristic of a structural element, and (B) an exemplary plot of force and electrical resistance as a function of displacement.
Figure 7B:
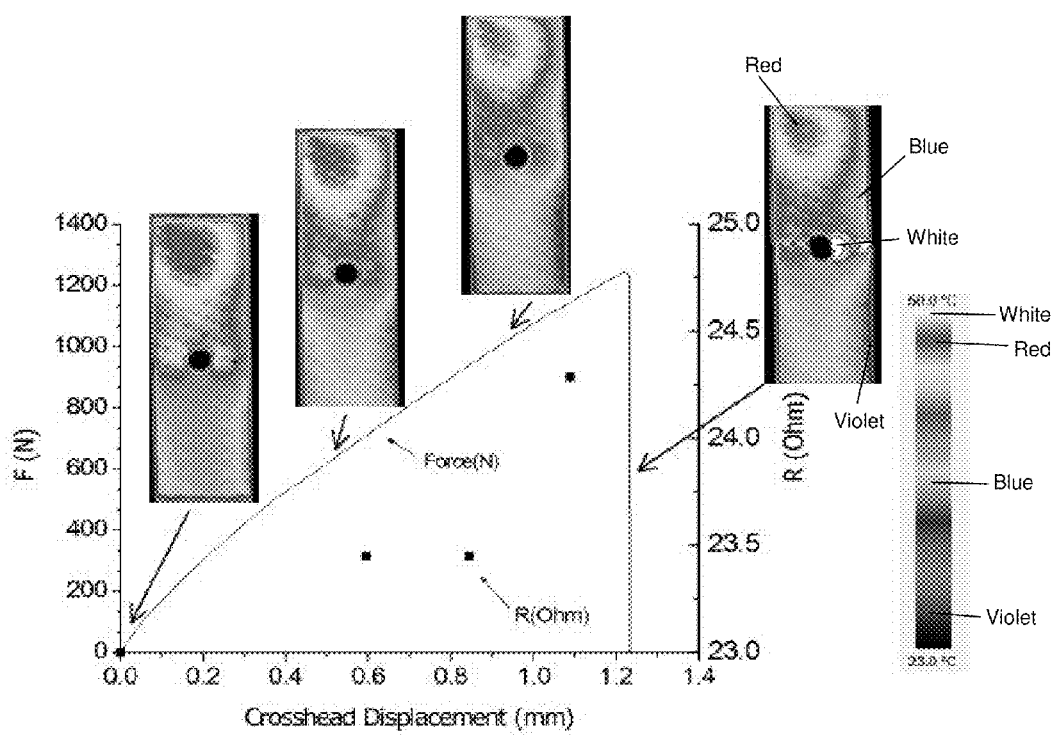

Each end of the composite was fixed, and a tensile load was applied using a standard uniaxial mechanical testing machine that allows displacement and force to be applied in a single direction, as illustrated in FIG. 7A. The sample was strained at a velocity of 0.2 mm/s, and thermographs were taken every 30 seconds with a thermal camera (PCE TC-3) placed approximately 0.5 m from the sample. FIG. 7B includes a plot of the applied force and resultant resistance as a function of the crosshead displacement of the specimen tested in this example. In addition, FIG. 7B includes exemplary thermographic images illustrating the temperature distribution on the sample at various stages of the test. A DC voltage of 6.8 V was applied, which initially yielded 0.3 A, increasing the maximum temperature of the sample 20° C. above room temperature. Before the test, the temperature was somewhat unevenly distributed across the sample, perhaps due to inhomogeneities in the sample during fabrication. The hottest areas observed were relatively close to the positive electrode and at both sides of the hole. The resistance increased during the test, reducing the current intensity along the test and the sample temperature, perhaps due to strain on the network of CNTs. The temperature distribution of the sample changed with the strain of the sample, an effect that was pronounced on both sides of the hole. Once the sample began to fail, flaws appeared clearly on the thermograph, and the temperature of the regions that were not completely broken apart were observed to increase. The average temperature on the right side of the hole from the beginning of the test until 1 mm of sample deformation, decreased 1.1° C. Meanwhile, the left side decreased 2.8° C. The differences in temperature variation might correspond with an increment in damage on that left side of the sample, producing damage to the sample first in that region. As a comparison, the temperature change in the same deformation range was the same above and below the hole (2.1° C., for both regions).

Example 4

Figure 8A:
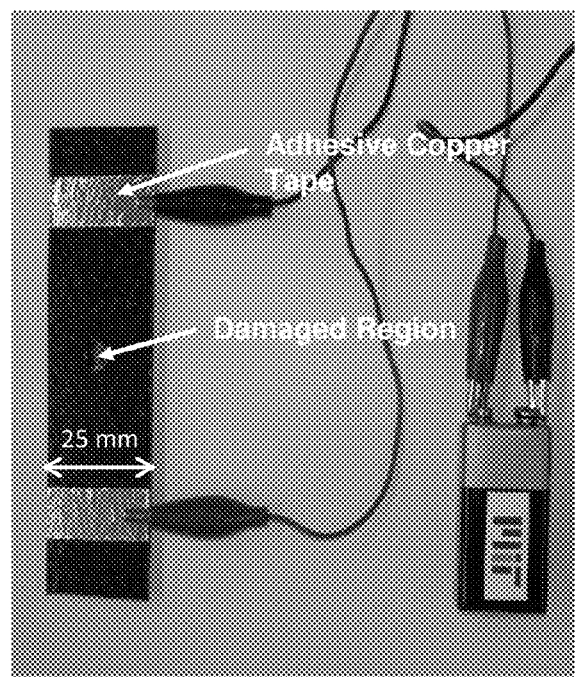
FIGS. 8A-8D include (A) a photograph of an exemplary damaged specimen, (B) an exemplary thermograph of the damaged specimen of FIG. 8A, (C) an exemplary photograph of a double-cantilever beam (DCB) specimen, and (D) an exemplary thermograph of the DCB specimen of FIG. 8C.
Figure 8B:
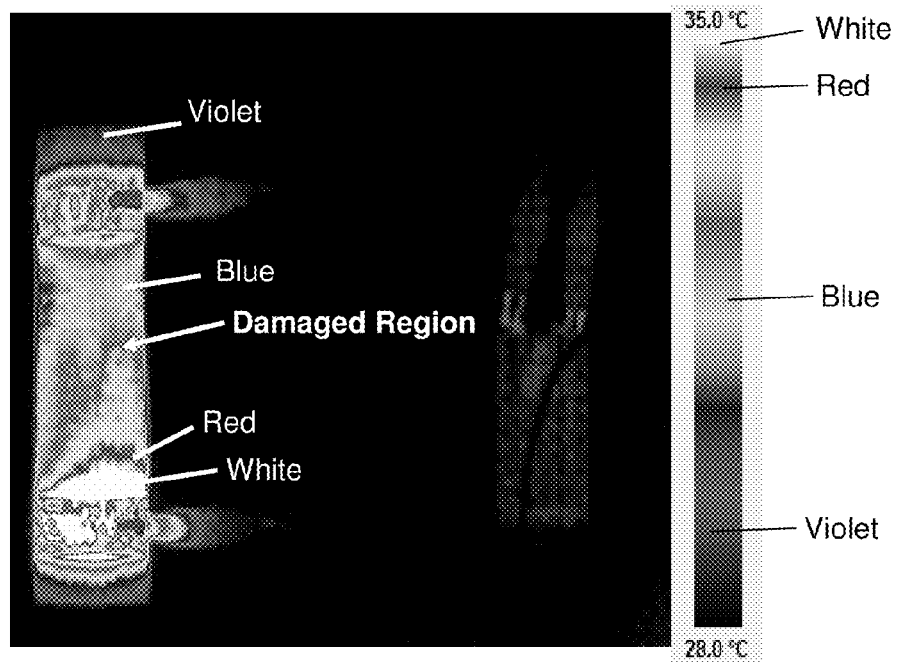

This example describes the evaluation of damage within various articles. In the first set of experiments, a nano-engineered composite comprising fuzzy fiber alumina cloth and epoxy resin was damaged on its surface with a blunt round tip hammered in the middle of the sample. Electrical contacts were made by sticking copper adhesive tape contacts on both sides of the sample. Current was applied thought alligator clamps attached to the specimen and on a 9V alkaline battery (Duracel), as shown in FIG. 8A. A thermograph, shown in FIG. 8B, was recorded with an infrared camera. The temperature of the heated region was about 17° C. above room temperature. In addition, the damaged region included a relatively low-temperature area. As was observed in Example 3, the positive electrode was hotter than the negative electrode.

Figure 8C:
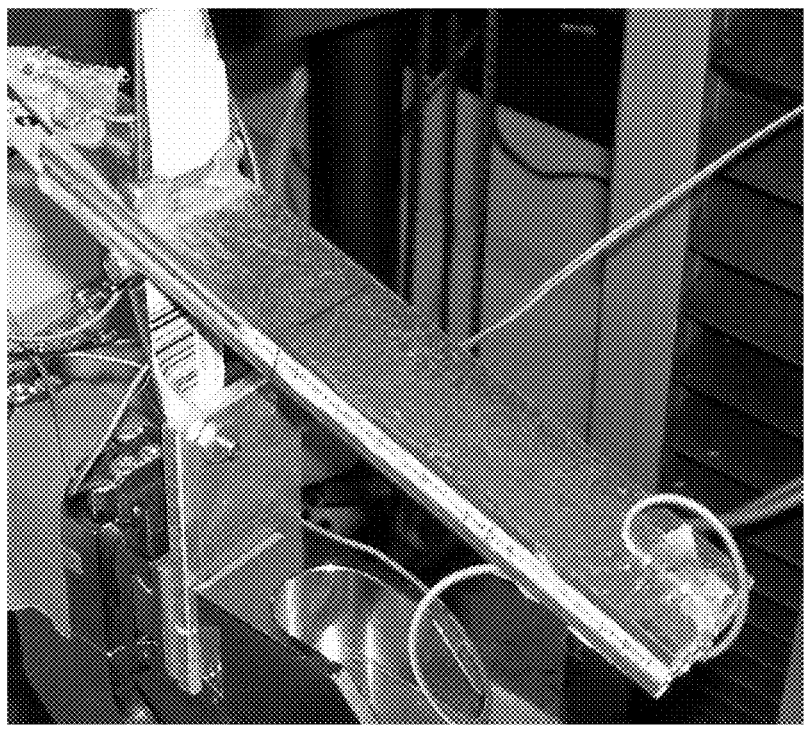
Figure 8D:
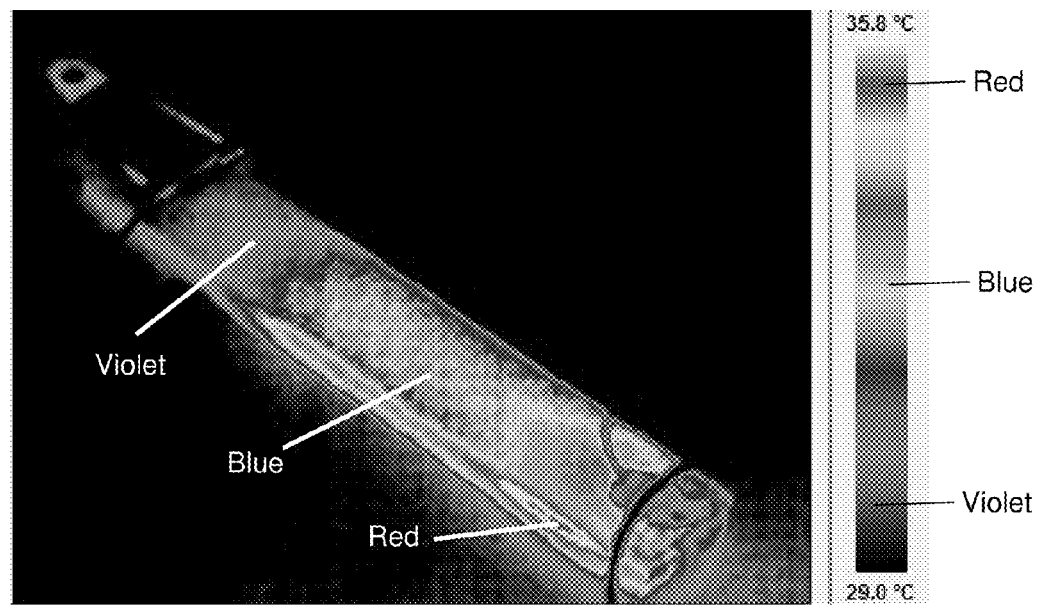

Another set of experiments were performed to determine whether a defect within the interior of a sample could be detected using thermography and resistive heating. In this set of experiments, an internal crack was created in a FFRP specimen by placing a Teflon film between two plies to create a double-cantilever beam (DCB) specimen. A photograph of the specimen is shown in FIG. 8C. This specimen was covered by two electrically insulating glass/epoxy plates glued on its surface as part of the fracture testing, and which may have acted to shield the heat radiation. Two opposite sides of the specimen were painted with silver paint, and wires were connected with silver paste. The thermal camera was placed at 0.5 m from the sample, focusing on the top surface and its section. A thermograph of the heated specimen is shown in FIG. 8D. On the bottom surface, the temperature distribution appeared to be homogeneous, with the exception of the crack region, where the temperature decreased. In this case, the heat may have propagated from the conductive FFRP layers heated by Joule effect to the non conductive layers, until reaching the surface of the sample. In the cross section, the crack was clearly noticed, and a hot temperature zone appeared on the end of the sample. The hot zone may have on the end of the sample may have been associated with the heat distribution and the proximity of the positive contact, and might not have been related with to a defect in the sample.

Example 5

This example describes the detection of a kissing-debond in a composite sample. The nano-engineered composite specimen included two plies of fuzzy fiber alumina cloth within cured epoxy resin positioned between two external plies of alumina fiber within cured epoxy resin. A thin-film Teflon layer was placed along the centerline on the last 2 inches of the laminate to form an initial pre-crack. The composite specimens were made using the hand lay-up method described in Example 2.

Figure 9A:
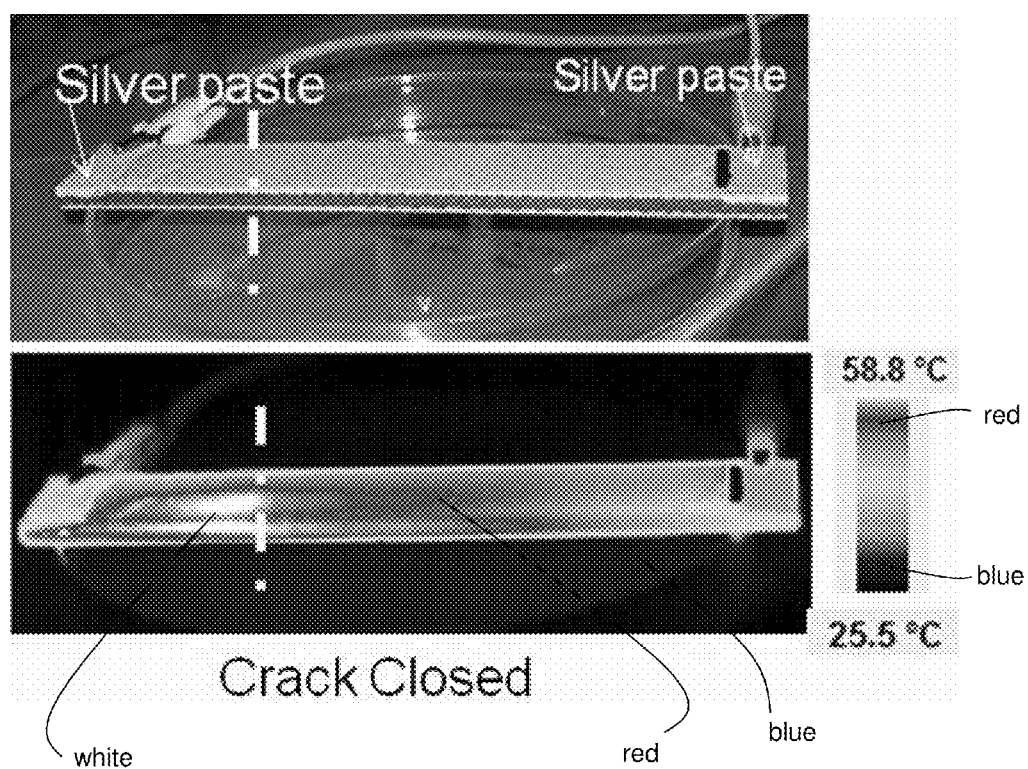
FIGS. 9A-9C include photographs of various arrangements of samples comprising kissing debonds, according to one set of embodiments.
Figure 9B:
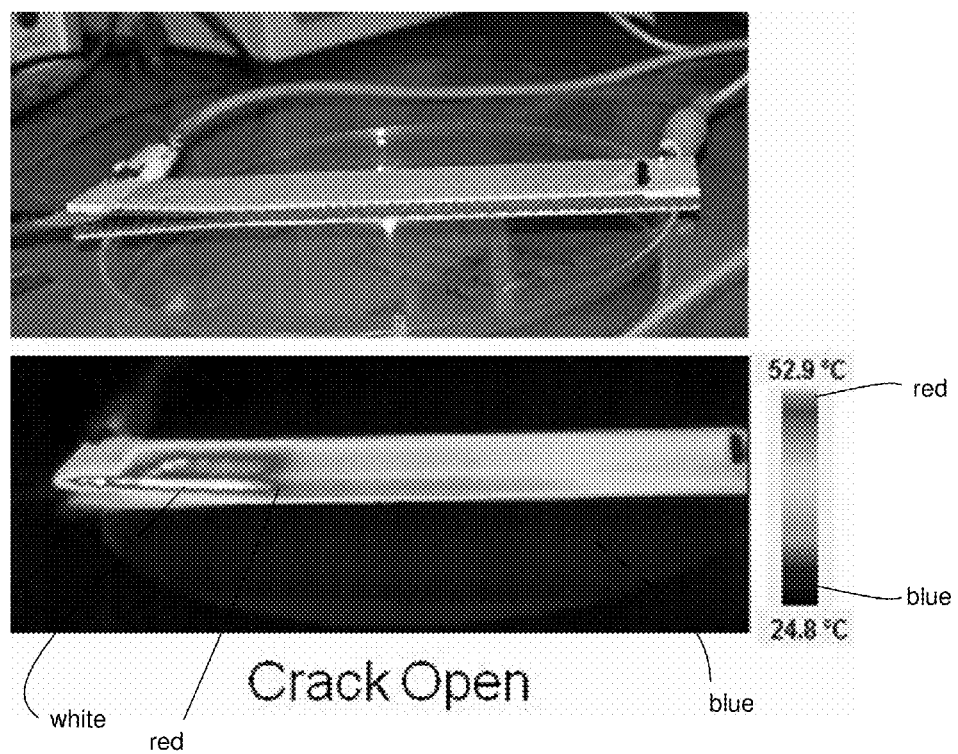
Figure 9C:
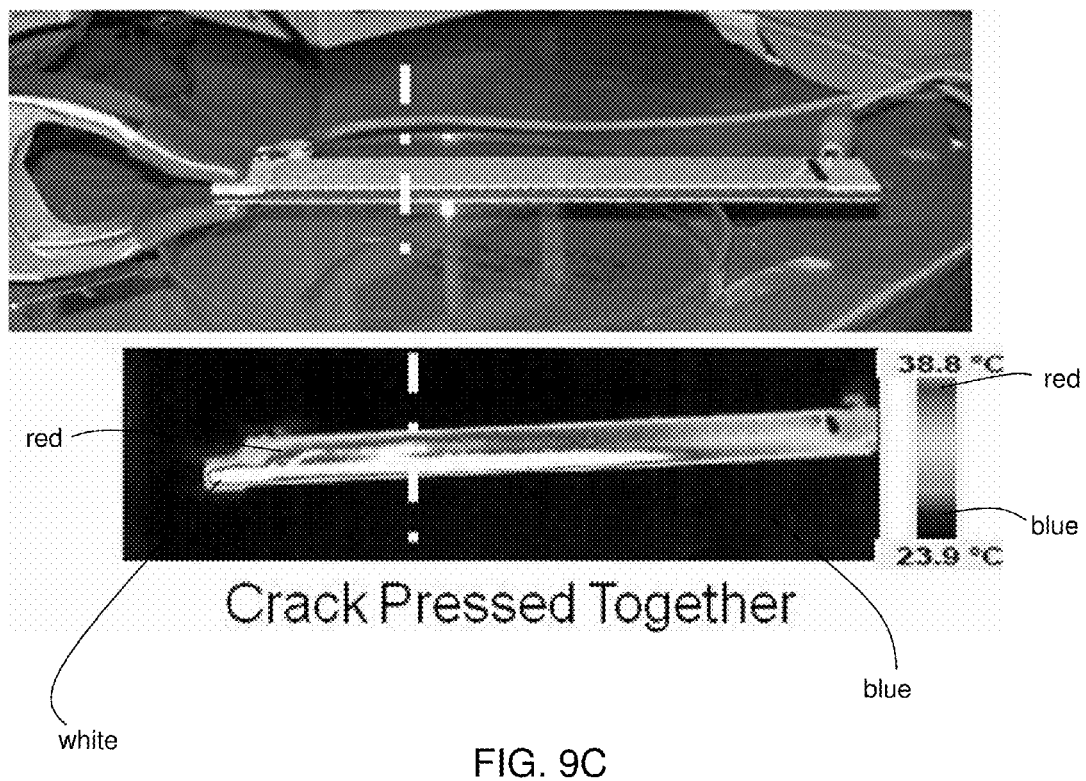

Conductive contacts were painted with silver paste on each side of the specimen, as shown in FIG. 9A. The sample was heated using a power supply (0.4 A, 25 V). In order to simulate a kissing debond, two set ups were performed: "crack closed" as indicated above, "crack pressed together", where both sides of the crack were pressed with a clamp, as can be seen in FIG. 9C. A control set up "crack open" (FIG. 9B) was prepared opening both sides of the crack.

When the samples were heated, a high temperature region corresponding to the kissing debond crack was observed in each of the "crack closed," "crack open," and "crack pressed together" arrangements. The high temperature region was observed on the both lateral sides and on the top and bottom faces of the sample. The difference in temperature obtained between the crack region and the rest of the sample was about 1° C. for the "crack pressed together" arrangement and about 5° C. for the "crack closed" arrangement.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system, comprising:
   a structural element comprising a network of electrically conductive nanostructures substantially uniformly distributed within the bulk of a primary structural material of the structural element;
   an electrical circuit comprising at least a portion of the network; and
   a sensor constructed and arranged to determine a first temperature of the structural element and/or of the network, wherein the system is constructed and arranged to pass an electrical current through the electrical circuit.

2. A system as in claim 1, wherein the first temperature is indicative of a mechanical characteristic of the structural element and/or of the network.

3. A system as in claim 1, wherein the network of electrically conductive nanostructures comprises a plurality of nanostructures, each of the nanostructures having an aspect ratio of at least 3 and a long axis.

4. A system as in claim 3, wherein the long axes of the nanostructures are substantially aligned.

5. A system as in claim 1, wherein the primary structural material comprises a material having an electrical resistivity of at least 100 Ohm·m at 20° C.

6. A system as in claim 5, wherein the primary structural material comprises at least one of a monomer, a polymer, a fiber, and a ceramic.

7. A system as in claim 5, wherein the primary structural material has an electrical resistivity of between 100 Ohm m and $1 \times 10^{30}$ Ohm m.

8. A system as in claim 1, wherein the primary structural material comprises a material that is electrically conductive.

9. A system as in claim 8, wherein the primary structural material comprises a metal.

10. A system as in claim 1, wherein the nanostructures comprise nanotubes.

11. A system as in claim 1, wherein the nanostructures comprise carbon-based nanostructures.

12. A system as in claim 1, wherein the nanostructures comprise carbon nanotubes.

13. A system as in claim 1, wherein the nanostructures comprise single-walled carbon nanotubes.

14. A system as in claim 1, wherein the nanostructures comprise multi-walled carbon nanotubes.

15. A system as in claim 1, wherein the nanostructures comprise metal nanoparticles.

16. A system as in claim 1, wherein the nanostructures comprise carbon nanowires.

17. A system as in claim 1, wherein the nanostructures comprise carbon black.

18. A system as in claim 1, wherein the nanostructures comprise graphite.

19. A system as in claim 1, wherein the nanostructures comprise carbon nanofibers.

20. A system as in claim 1, wherein the nanostructures comprise graphene nanoparticles.

21. A system as in claim 1, wherein the nanostructures comprise metal nanowires.

22. A system as in claim 1, wherein the electrically conductive nanostructures have an electrical resistivity of less than 0.1 Ohm m.

23. A system as in claim 1, wherein the structural element comprises a plurality of electrical contacts to which electrical leads can be applied, and through which electrical current can be passed.

24. A system as in claim 1, wherein the sensor is constructed and arranged to determine a first temperature of the structural element and/or of the network indicative of resistive heating of the network.

25. A method, comprising:
passing an electrical current through at least a portion of a network of electrically conductive nanostructures substantially uniformly distributed within the bulk of a primary structural material of a structural element;
determining a first temperature of the structural element using a sensor; and
determining a mechanical characteristic of the structural element and/or of the network based at least in part upon the first temperature of the structural element.

26. A method as in claim 25, wherein determining the mechanical characteristic of the structural element and/or of the network comprises determining the location of the mechanical characteristic.

27. A method as in claim 25, wherein determining the mechanical characteristic of the structural element and/or of the network comprises determining the size of the mechanical characteristic.

28. A method as in claim 25, wherein determining the mechanical characteristic of the structural element and/or of the network comprises determining the presence or absence of an elastic deformation.

29. A method as in claim 25, wherein determining a mechanical characteristic of the structural element and/or of the network comprises determining the presence or absence of a plastic deformation.

30. A method as in claim 25, wherein determining a mechanical characteristic of the structural element and/or of the network comprises determining the presence or absence of a fracture.

31. A method as in claim 25, wherein determining a mechanical characteristic of the structural element and/or of the network comprises determining the presence or absence of a dislocation.

32. A method as in claim 25, wherein determining a mechanical characteristic of the structural element and/or of the network comprises determining the presence or absence of an inclusion.

33. A method as in claim 25, wherein the mechanical characteristic of the structural element is located on an external surface of the structural element.

34. A method as in claim 25, wherein the mechanical characteristic of the structural element is located within the bulk of the structural element.

35. A method as in claim 25, wherein the mechanical characteristic of the structural element has a maximum cross-sectional dimension of less than 100 mm.

36. A method as in claim 25, wherein the first temperature is at least 0.01° C. higher than an ambient temperature.

37. A method as in claim 25, wherein the first temperature is produced in the absence of a substantial source of heat external to the network of electrically conductive nanostructures.

38. A method as in claim 25, wherein the first temperature is produced in the absence of a substantial source of heat external to the structural element.

39. A method as in claim 25, wherein determining a mechanical characteristic of the structural element comprises comparing the first temperature of the structural element to a second temperature.

40. A method as in claim 39, wherein the first temperature is determined at a first location on or within the structural element, and the second temperature is determined at a second location on or within a different part of the structural element.

41. A method as in claim 39, wherein the first and second temperatures are determined at different times.

42. A method as in claim 39, wherein the second temperature value is determined prior to first use of the structural element.

43. A method as in claim 39, wherein the second temperature value is determined after use of the structural element.

44. A method as in claim 25, wherein determining a temperature comprises determining a distribution of multiple temperatures on or within the structural element.

45. A method as in claim 25, wherein determining a temperature comprises determining a continuous gradient of temperatures across a line or surface on or within the structural element.

46. A method as in claim 25, wherein determining a temperature comprises determining a discontinuous gradient of temperatures across a line or surface on or within the structural element.

47. A method as in claim 25, wherein passing an electrical current through the network of electrically conductive nanostructures resistively heats the structural element.

48. A method as in claim 25, wherein an imaging device is used to determine the first temperature of the structural element.

49. A method as in claim 25, wherein at least one of a thermographic camera, a thermocouple, a thermal indicator film, a piezoresistive temperature sensor, a piezoelectric temperature sensor, or a thermoelectric temperature sensor is used to determine the first temperature of the structural element.

50. A method as in claim 25, wherein passing the electrical current through at least a portion of the network of electrically conductive nanostructures comprises establishing a voltage difference of less than 100 Volts across at least a portion of the network of electrically conductive nano structures.

51. A method as in claim 25, wherein passing an electrical current through at least a portion of the network of electrically conductive nanaostructures comprises applying a first electrical current across a first pair of two locations defining a first direction, and applying a second electrical current across a second pair of two locations defining a second direction.

52. A method as in claim 51, wherein the first and second electrical currents are applied at different times.

53. A method as in claim 51, wherein the first and second electrical currents are applied at the same time.

54. A method as in claim 25, wherein passing the electrical current through at least a portion of the network of electrically conductive nanostructures comprises application of a power of less than 100 Watts.

55. A method as in claim 25, wherein the electrical current comprises direct current.

56. A method as in claim 25, wherein the electrical current comprises alternating current.

57. A method as in claim 25, wherein the electrical current comprises direct current and alternating current.

58. A method as in claim 25, wherein the electrical current is passed from one end of the structural element to another end of the structural element.

59. A method as in claim 25, wherein the electrical current is passed through only a portion of the structural element.

60. A method as in claim 25, wherein determining a mechanical characteristic of the structural element and/or of the network comprises determining a mechanical defect of the structural element and/or of the network.

61. A method, comprising:
passing an electrical current through at least a portion of a network of electrically conductive nanostructures substantially uniformly distributed within the bulk of a primary structural material of a structural element, the primary structural material having an electrical resistivity of at least 100 Ohm·m at 20° C.; and
determining a first temperature of the structural element and/or of the network using a sensor, indicative of resistive heating of the network, thereby determining a mechanical characteristic of the structural element indicative of a mechanical transformation.

62. A method as in claim 61, wherein determining a mechanical characteristic of the structural element indicative of a mechanical transformation comprises determining a mechanical defect of the structural element.

63. A method, comprising:
passing an electrical current through at least a portion of a structural element formed of a primary structural material having an electrical resistivity of at least 100 Ohm·m at 20° C., wherein the structural element comprises a network of electrically conductive nanostructures substantially uniformly distributed within the bulk of the primary structural material;
determining a first temperature of the structural element using a sensor; and
determining a mechanical characteristic of the structural element indicated by the first temperature of the structural element.

64. A method as in claim 63, wherein determining a mechanical characteristic of the structural element comprises determining a mechanical defect of the structural element.

* * * * *